(12) United States Patent
Kuzma et al.

(10) Patent No.: US 7,960,335 B2
(45) Date of Patent: Jun. 14, 2011

(54) OCTREOTIDE IMPLANT HAVING A RELEASE AGENT AND USES THEREOF

(75) Inventors: Petr Kuzma, Princeton, NJ (US); Stefanie Decker, Princeton, NJ (US); Harry Quandt, Bensalem, PA (US)

(73) Assignee: Endo Pharmaceuticals Solutions Inc., Chadds Ford, PA (US)

( * ) Notice: Subject to any disclaimer, the term of this patent is extended or adjusted under 35 U.S.C. 154(b) by 0 days.

(21) Appl. No.: 12/490,979

(22) Filed: Jun. 24, 2009

(65) Prior Publication Data
US 2010/0022450 A1 Jan. 28, 2010

Related U.S. Application Data

(60) Provisional application No. 61/075,625, filed on Jun. 25, 2008, provisional application No. 61/080,144, filed on Jul. 11, 2008.

(51) Int. Cl.
*A61K 38/00* (2006.01)
*A61K 9/52* (2006.01)
(52) U.S. Cl. ......... 514/1.1; 514/21.7; 424/422; 424/460
(58) Field of Classification Search ........................ None
See application file for complete search history.

(56) References Cited

U.S. PATENT DOCUMENTS

| | | | |
|---|---|---|---|
| 2,513,014 A | 6/1950 | Fields | |
| 3,921,632 A | 11/1975 | Bardani | |
| 4,131,604 A | 12/1978 | Szycher | |
| 4,285,987 A | 8/1981 | Ayer et al. | |
| 4,298,002 A | 11/1981 | Ronel et al. | |
| 4,386,039 A | 5/1983 | Szycher | |
| 4,523,005 A | 6/1985 | Szycher | |
| 4,743,673 A | 5/1988 | Johnston et al. | |
| 4,751,133 A | 6/1988 | Szycher et al. | |
| 4,846,793 A | 7/1989 | Leonard et al. | |
| 4,871,094 A | 10/1989 | Gall et al. | |
| 4,954,587 A | 9/1990 | Mueller | |
| 4,959,217 A | 9/1990 | Sanders et al. | |
| 4,994,028 A | 2/1991 | Leonard et al. | |
| 5,004,614 A | 4/1991 | Staniforth | |
| 5,035,891 A | 7/1991 | Runkel et al. | |
| 5,254,662 A | 10/1993 | Szycher et al. | |
| 5,266,325 A | 11/1993 | Kuzma et al. | |
| 5,273,752 A | 12/1993 | Ayer et al. | |
| 5,292,515 A | 3/1994 | Moro et al. | |
| 5,342,622 A | 8/1994 | Williams et al. | |
| 5,354,835 A | 10/1994 | Blair | |
| 5,431,921 A | 7/1995 | Thombre | |
| 5,464,933 A | 11/1995 | Bolognesi et al. | |
| 5,468,811 A | 11/1995 | Moro et al. | |
| 5,614,223 A | 3/1997 | Sipos | |
| 5,637,309 A | 6/1997 | Tajima et al. | |
| 5,686,411 A | 11/1997 | Gaeta et al. | |
| 5,756,127 A | 5/1998 | Grisoni et al. | |
| 5,817,343 A | 10/1998 | Burke | |
| 5,854,127 A | 12/1998 | Pan | |
| 5,876,761 A | 3/1999 | Bodmer et al. | |
| 5,894,458 A | 4/1999 | Takizawa et al. | |
| 6,087,334 A | 7/2000 | Beeley et al. | |
| 6,143,718 A | 11/2000 | Kolterman et al. | |
| 6,159,490 A | 12/2000 | Deghenghi | |
| 6,313,254 B1 | 11/2001 | Meijs et al. | |
| 6,337,318 B1 | 1/2002 | Trigg et al. | |
| 6,361,797 B1 | 3/2002 | Kuzma et al. | |
| 6,417,164 B1 | 7/2002 | Kolterman et al. | |
| 6,579,851 B2 | 6/2003 | Goeke et al. | |
| 6,602,694 B1 | 8/2003 | Albrandt et al. | |
| 6,770,623 B1 | 8/2004 | Chang et al. | |
| 6,872,700 B1 | 3/2005 | Young et al. | |
| 6,942,264 B1 | 9/2005 | Mendez | |
| 6,969,480 B2 | 11/2005 | Dalton et al. | |
| 7,008,927 B2 | 3/2006 | Ochiai et al. | |
| 7,056,887 B2 | 6/2006 | Coolidge et al. | |
| 7,101,853 B2 | 9/2006 | Young et al. | |
| 7,105,489 B2 | 9/2006 | Hathaway | |
| 7,115,569 B2 | 10/2006 | Beeley et al. | |
| 7,118,737 B2 | 10/2006 | Kochendoerfer et al. | |
| 7,153,825 B2 | 12/2006 | Young et al. | |
| 7,220,721 B1 | 5/2007 | Beeley et al. | |
| 7,259,136 B2 | 8/2007 | Hathaway et al. | |
| 7,271,238 B2 | 9/2007 | Gaeta et al. | |
| 7,452,868 B2 | 11/2008 | Kuzma et al. | |
| 2002/0141985 A1 | 10/2002 | Pittner et al. | |
| 2003/0036504 A1 | 2/2003 | Kolterman et al. | |
| 2004/0002454 A1 | 1/2004 | Coolidge et al. | |
| 2004/0097419 A1 | 5/2004 | Petersen et al. | |

(Continued)

FOREIGN PATENT DOCUMENTS

EP   0 246 653 A2   11/1987

(Continued)

OTHER PUBLICATIONS

U.S. Appl. No. 12/490,971, filed Jun. 24, 2009, Kuzma et al.
"RxMed: Pharmaceutical Information-Sandostatin LAR DEPOT" [online], Jan. 6, 2003 [retrieved Aug. 16, 2006]; http://www.rxmed.com.
A.R. Gennaro, Remington: The Science and Practice of Pharmacy, 19th Edition, p. 1662, 1995.
Barradell, L. B. et al., "Histrelin: A Review of its Pharmacological Properties and Therapeutic Role in Central Precocious Puberty," Drugs, vol. 45, No. 4, Apr. 1993, pp. 570-588; published by Adis International Limited.
Berge, et al., "Pharmaceutical Salts," Journal of Pharmaceutical Sciences, vol. 66, No. 1, Jan. 1977, pp. 1-19.
Bevan et al., Primary Medical Therapy for Acromegaly: An Open, Prospective, Multicenter Study of the Effects of Subcutaneous and Intramuscular Slow-Release Octreotide on Growth Hormone, Insulin-Like Growth Factor-L, and Tumor Size, J. Clin. Endoc. Metab,. 87(10), 2002, pp. 4554-4563.
Chinese Office Action corresponding to CN 2006800160292, dated Sep. 4, 2009, 8 pages.

(Continued)

*Primary Examiner* — Robert Landsman
*Assistant Examiner* — Gyan Chandra
(74) *Attorney, Agent, or Firm* — Gilberto M. Villacorta; Jeffrey R. Lomprey; Foley & Lardner LLP

(57) ABSTRACT

Methods, formulations and kits are described that allow for the controlled release of octreotide, e.g., octreotide acetate, in a subject.

28 Claims, 21 Drawing Sheets

U.S. PATENT DOCUMENTS

| | | | |
|---|---|---|---|
| 2005/0037078 A1 | 2/2005 | Kuo et al. | |
| 2005/0143303 A1 | 6/2005 | Quay et al. | |
| 2005/0287320 A1 | 12/2005 | Dalton et al. | |
| 2006/0019903 A1 | 1/2006 | Kuzma et al. | |
| 2006/0030528 A1 | 2/2006 | Hathaway et al. | |
| 2006/0035836 A1 | 2/2006 | Coolidge et al. | |
| 2006/0067911 A1 | 3/2006 | Nilsson et al. | |
| 2006/0122106 A1 | 6/2006 | Gedulin et al. | |
| 2006/0148713 A1 | 7/2006 | Beeley et al. | |
| 2006/0204540 A1* | 9/2006 | Kuzma et al. | 424/423 |
| 2006/0233747 A1 | 10/2006 | Kochendoerfer et al. | |
| 2006/0293232 A1 | 12/2006 | Levy et al. | |
| 2007/0010656 A1 | 1/2007 | Beeley et al. | |
| 2008/0311170 A1 | 12/2008 | Kuzma et al. | |
| 2009/0035343 A1 | 2/2009 | Kuzma et al. | |
| 2009/0087470 A1 | 4/2009 | Kuzma et al. | |

FOREIGN PATENT DOCUMENTS

| | | |
|---|---|---|
| EP | 0 314 206 B1 | 5/1989 |
| EP | 0 384 646 A1 | 8/1990 |
| EP | 0 551 699 A1 | 7/1993 |
| EP | 0 645 136 A2 | 3/1995 |
| FR | 821383 A | 12/1937 |
| GB | 1 306 541 A | 2/1973 |
| JP | 05-269759 A | 10/1993 |
| JP | 05-269760 A | 10/1993 |
| JP | 07-097338 A | 4/1995 |
| JP | 07-252166 A | 10/1995 |
| JP | 11-506730 A | 6/1999 |
| JP | 2002-535452 A | 10/2002 |
| NZ | 245383- | 5/1994 |
| WO | WO-96/40049 A1 | 12/1996 |
| WO | WO-98/44964 A1 | 10/1998 |
| WO | WO-00/44356- | 8/2000 |
| WO | WO-02/49573 A2 | 6/2002 |
| WO | WO-02/078597 A2 | 10/2002 |
| WO | WO-2004/071736 A2 | 8/2004 |
| WO | WO-2005/013936 A2 | 2/2005 |
| WO | WO-2005/041873 A2 | 5/2005 |
| WO | WO-2006/099288 A3 | 9/2006 |
| WO | WO-2007/028394 A2 | 3/2007 |
| WO | WO-2008/061355 A1 | 5/2008 |
| WO | WO-2008/134475 A2 | 11/2008 |

OTHER PUBLICATIONS

Eurasian Patent Office Decision on Patentability corresponding to EU 200701956/28, dated Jan. 21, 2009, 6 pages.

New Zealand Patent Office Examination Report corresponding to NZ 561400, dated Jul. 28, 2009, 2 pages.

Feuillan, P. P. et al., "Follow-up of children and young adults after GnRH-agonist therapy for central precocious puberty," J. Endocrinol. Invest., vol. 24, 2001, pp. 734-736; published by Editrice Kurtis.

Higuchi, et al., Pro-Drugs as Novel Drug Delivery Systems: A.C.S Symposium Series, American Chemical Society, Washington, DC, 1975.

International Search Report and Written Opinion, PCT/US2009/050215, dated Nov. 25, 2009, 11 pgs.

International Search Report, PCT/US00/01664, dated Jul. 13, 2000, 1 pg.

International Search Report, PCT/US06/08891, dated Dec. 4, 2006, 2 pgs.

International Search Report, PCT/US2005/021368, dated Oct. 23, 2006, 3 pgs.

International Search Report, PCT/US2008/061511, dated Nov. 8, 2009, 2 pgs.

Lan NaLee, "Volume of Blood in a Human," from http://hypertextbook.com/facts/1998/LanNaLee.shtml, (1998) updated (2001).

Langer, "Implantable Controlled Release Systems," Pharmac. Ther. (1983), vol. 21, p. 35-51.

P. Kuzma et al., U.S. PTO Office Action, U.S. Appl. No. 11/155,822 dated Jan. 22, 2008, 12 pgs.

P. Kuzma et al., U.S. PTO Office Action, U.S. Appl. No. 11/155,822 dated Feb. 18, 2009, 11 pgs.

P. Kuzma et al., U.S. PTO Office Action, U.S. Appl. No. 11/155,822 dated Oct. 13, 2009, 21 pgs.

Palii et al., "Medical treatment of diabetic retinopathy with somatostatin analogues," Expert Opinion Investig. Drugs, vol. 16, No. 1, (2007), pp. 73-82.

Pawlikowski et al., "Perspectives of new potential therapeutic applications of somatostatin analogs," Neuroendocrinology Letters, vol. 24, Nos. 1/2, Feb.-Apr. 2003, pp. 21-27.

Pierard-Franchimont et al., "Incidental Control of Rosacea by Somatostatin," Dermatology, (2003) 206:249-251.

Roche, ed., Bioreversible Carriers in Drug Design: Theory and Application, Pergamon Press, New York, 1987.

American Peptide Company, Inc., Peptide Catalog 2006-2007, pp. 119, 171, 175, 211, 217, 219, 227, 296, 315, 317 and 329.

Bodmer D., et al: "Factors influencing the release of peptides and proteins from biodegradable parenteral depot systems" Journal of Controlled Release, Elsevier, Amsterdam, NL LNKD-DOI:10.1016/0168-3659(92)90014-I, vol. 21, No. 1-3, Jul. 1, 1992 , pp. 129-137, XP025702099 ISSN: 0168-3659 [retrieved on Jul. 1, 1992].

European Search Report for EP/00904513, completed Mar. 27, 2003.

European Search Report for EP/92300394, completed Sep. 28, 1992.

European Search Report for EP/92300395, dispatched Feb. 27, 1995.

International Search Report (PCT/US2009/048475) dated Jun. 1, 2010.

International Search Report and Written Opinion for PCT/US2009/048484 dated Nov. 26, 2009.

Notice of Allowance for U.S. Appl. No. 12/240,690, mail date Mar. 26, 2010.

Notice of Allowance for U.S. Appl. No. 11/372,749, mail date Aug. 11, 2008.

Notice of Allowance for U.S. Appl. No. 12/171,999, mail date Mar. 22, 2010.

O'Donnell, et al "Therapeutic Potential of a Long Acting Somatostatin Analogue in Gastrointestinal Diseases" GUT, 1989, vol. 30, pp. 1165-1172.

Office Action for U.S. Appl. No. 07/589,957, mail date Oct. 17, 1991.

Office Action for U.S. Appl. No. 11/155,822, mail date Jul. 8, 2010.

Office Action for U.S. Appl. No. 11/372,749, mail date Feb. 5, 2008.

Office Action for U.S. Appl. No. 12/490,971, mail date Sep. 14, 2010.

P. E. Nielsen et al., "Peptide Nucleic Acid (PNA). A DNA Mimic with a Peptide Backbone," Bioconjugate Chem., vol. 5, No. 1, 1994, pp. 3-7.

Prommer, "Established and Potential Therapeutic Applications of Octreotide in Palliative Care", Support Care Cancer, 2008, vol. 16, pp. 1117-1123.

Refojo, M. F., et al., "Microscopic Determination of the Penetration of Proteins and Polysaccharides into Poly(hydroxyethyl Methacrylate) and similar Hydrogels," Journal of Polymer Science, Polymer Symposium, vol. 66, (1979), pp. 227-237.

Remington's Pharmaceutical Sciences, Osol., A. ed., Mack Publishing Co., (1980).

S. W. Kim et al., "Water in Polymers—Solute Permeation Through Hydrogel Membranes," ACS Symposium Series, 127 (1980). pp. 347-359.

Spitz, et al. "GnRH Superanalog Implants for Prostate Cancer" Proceedings of the 12th International Congress of Endocrinology, 2004, pp. 389-395.

Supplementary European Search Report for EP/67838004, completed Jun. 23, 2010.

Chertin et al., "An Implant Releasing the Gonadotropin Hormone-Releasing Hormone Agonist Histrelin Maintains Medical Castration for Up to 30 Months in Metastic Prostate Cancer," Journal of Urology, Baltimore, MD, US, vol. 163, Mar. 2000. pp. 838-844.

Schlegel et al., "Effective Long-Term Androgen Suppression in Men with Prostate Cancer Using a Hydrogel Implant with the GnRH Agonist Histrelin," Urology, vol. 58, 2001, pp. 578-582.

* cited by examiner

OCTREOTIDE IMPLANT HAVING A RELEASE AGENT AND USES THEREOF

RELATED APPLICATIONS

This application claims the benefit of U.S. Provisional Application 61/075,625, filed Jun. 25, 2008, and U.S. Provisional Application 61/080,144, filed Jul. 11, 2008. The entire contents of each of these applications is incorporated herein by reference.

BACKGROUND

Acromegaly is a hormonal disorder that results when the pituitary gland produces excess growth hormone (GH). It most commonly affects middle-aged adults and can result in serious illness and premature death. Once diagnosed, acromegaly is treatable in most patients, but because of its slow and often insidious onset, it frequently is not diagnosed correctly. The most serious health consequences of acromegaly are diabetes mellitus, hypertension and increased risk of cardiovascular disease. Patients with acromegaly are also at increased risk for polyps of the colon that can develop into cancer. When GH-producing tumors occur in childhood, the disease that results is called gigantism rather than acromegaly. Fusion of the growth plates of the long bones occurs after puberty so that development of excessive GH production in adults does not result in increased height. Prolonged exposure to excess GH before fusion of the growth plates causes increased growth of the long bones and increased height.

Acromegaly is caused by prolonged overproduction of growth hormone (GH) by the pituitary gland. The pituitary is a small gland at the base of the brain that produces several important hormones to control body functions such as growth and development, reproduction, and metabolism. GH is part of a cascade of hormones that, as the name implies, regulates the physical growth of the body. This cascade begins in a part of the brain called the hypothalamus, which makes hormones that regulate the pituitary. One of these, GH-releasing hormone (GHRH), stimulates the pituitary gland to produce GH. Another hypothalamic hormone, somatostatin, inhibits GH production and release. Secretion of GH by the pituitary into the bloodstream causes the production of another hormone, called insulin-like growth factor 1 (IGF-1), in the liver. IGF-1 is the factor that causes the growth of bones and other tissues of the body. IGF-1, in turn, signals the pituitary to reduce GH production. GHRH, somatostatin, GH and IGF-1 levels in the body are tightly regulated by each other, and their levels are influenced by environmental stimuli such as sleep, exercise, stress, food intake and blood sugar levels. If the pituitary produces GH independent from the normal regulatory mechanisms, the level of IGF-1 would rise, leading to bone growth and organ enlargement. Excess GH also causes changes in sugar and lipid metabolism and can cause diabetes.

In over 90% of acromegaly patients, the overproduction of GH is caused by a benign tumor of the pituitary gland, called an adenoma. These tumors produce excess GH and, as they expand, compress surrounding brain tissues, such as the optic nerves. This expansion causes the headaches and visual disturbances that are often symptoms of acromegaly. In addition, compression of the surrounding normal pituitary tissue can alter production of other hormones, leading to changes in menstruation and breast discharge in women and impotence in men.

In some patients, acromegaly is caused not by pituitary tumors but by tumors of the pancreas, lungs and adrenal glands. These tumors lead to an excess of GH, either because they produce GH themselves or, more frequently, because they produce GHRH, the hormone that stimulates the pituitary to make GH. In these patients, the excess GHRH can be measured in the blood and establishes that the cause of the acromegaly is not due to a pituitary defect. When these nonpituitary tumors are surgically removed, GH levels fall and the symptoms of acromegaly improve.

Acromegaly treatment regimens include reducing GH production to normal levels to relieve the pressure that the growing pituitary tumor exerts on the surrounding brain areas, to preserve normal pituitary function, and to reverse or ameliorate the symptoms of acromegaly. Treatment options include surgical removal of the tumor, drug therapy and radiation therapy of the pituitary.

Octreotide has been demonstrated to be effective in the management of acromegaly. GH levels usually decrease within two hours following a subcutaneous octreotide injection. Octreotide results in a decrease in GH and IGF-1 levels in a majority of patients with normalization of IGF-1 levels in up to 60% of patients, indicating biochemical remission. Most patients note a marked improvement in their symptoms of acromegaly including headaches, joint pains and diaphoresis very soon after starting octreotide therapy. Octreotide is currently available as Sandostatin LAR® Depot, which is, upon reconstitution, a suspension of microspheres containing octreotide acetate. Sandostatin LAR® Depot is the only medication indicated for the long-term maintenance therapy in acromegalic patients. It is also indicated for the long-term treatment of severe diarrhea and flushing episodes associated with metastatic carcinoid tumors and profuse water diarrhea associated with VIP-secreting tumors. Sandostatin LAR® Depot is administered via intramuscular injection every four weeks, following a titration period. Octreotide acetate has also been available in an immediate-release formulation, Sandostatin® Injection solution, which is required to be administered by injection three times daily. In patients who do not have a significant reduction in GH levels in response to intermittent octreotide injections, more frequent dosing of octreotide may result in a greater clinical response. Octreotide may be administered continuously by a subcutaneous pump to patients with refractory acromegaly to prevent escape of GH between injections.

In light of the efficacy of octreotide for treating acromegaly and lack of a controlled-release treatment method and formulation of octreotide, there is a need for a formulation and delivery method that can deliver octreotide over a period of time at a controlled rate to avoid the complications of a patient's having to suffer, for example, multiple periodic injections. There is also a clear need for a formulation and delivery method that can deliver octreotide over a period of time at a controlled rate to effectively treat other disorders and conditions, and/or their associated symptoms, including conditions and disorders characterized by or related to increased levels of GH and IGF-1.

SUMMARY

The present invention relates generally to an octreotide pharmaceutical composition that can be used to treat individuals affected with hormonal disorders. Formulations described herein allow for the controlled release of one or more active agents, e.g., octreotide. The embodiments described herein are based on the unexpected discovery that octreotide can be released at a controlled rate using an implantable device. The formulations and methods described herein provide a therapeutically effective amount of octreotide over an extended period of time, e.g., about two months, about six months and up to about two years.

One embodiment is directed to a formulation for the controlled release of octreotide after implantation into a subject comprising a preparation substantially encased in a hydrophilic polymer selected from polyurethane based polymers and methacrylate based polymers, wherein the preparation comprises octreotide, wherein the formulation is effective to permit release of octreotide at a rate of about 30 µg to about 800 µg per day over about six months in vivo, and wherein the hydrophilic polymer but not the preparation further comprises a release agent with a molecular weight of at least about 1000 Daltons. In a particular embodiment, the release agent is a non-ionic surfactant, e.g., a polyethylene glycol hydrophilic tail and a lipophilic head. In a particular embodiment, the release agent is selected from the group consisting of: Brij 35, polyoxyethylene(20)sorbitan trioleate, Tween 20, Tween 80, Vitamin E TPGS, and a mixture of any two or more thereof. In a particular embodiment, the release agent has a molecular weight of at least about 1200 Daltons. In a particular embodiment, the hydrophilic polymer has an exterior surface area of about 350 mm2 or greater, e.g., from about 350 mm2 to about 1500 mm2. In a particular embodiment, the formulation permits release of octreotide at an average rate ranging from about 75 µg per day to about 300 µg per day in vivo. In a particular embodiment, the octreotide is octreotide acetate. In a particular embodiment, the hydrophilic polymer comprises a mixture of 2-hydroxyethyl methacrylate and hydroxypropyl methacrylate. In a particular embodiment, the formulation provides an in vivo average Css of about 0.1 ng/mL to about 9 ng/mL of octreotide in the subject. In a particular embodiment, the formulation provides an in vivo average Css of about 1 ng/mL to about 4 ng/mL of octreotide in the subject. In a particular embodiment, the preparation comprises about 40 mg to about 120 mg of octreotide, e.g., about 50 mg of octreotide acetate, about 85 mg of octreotide acetate. In a particular embodiment, the hydrophilic polymer comprises a mixture of about 20% of 2-hydroxyethyl methacrylate and about 80% hydroxypropylmethacrylate. In a particular embodiment, the hydrophilic polymer comprises a mixture of about 40% of 2-hydroxyethyl methacrylate and about 60% hydroxypropylmethacrylate. In a particular embodiment, the preparation further comprises an excipient selected from the group consisting of: magnesium stearate, stearic acid, vegetable stearin, talc and silica. In a particular embodiment, the preparation further comprises a compound selected from the group consisting of: hydroxypropylcellulose, hydroxyethyl cellulose, methyl cellulose, sodium carboxymethyl cellulose, modified starch and crosslinked polyvinyl pyrrolidone. In a particular embodiment, the hydrophilic polymer comprises a polyurethane-based polymer.

One embodiment is directed to a method of decreasing GH levels or IGF-1 levels in a subject and/or treating an octreotide-sensitive disease, disorder or symptom, e.g., acromegaly or symptoms associated with acromegaly, a symptom associated with a carcinoid tumor, VIPoma or neuroendocrine tumor, carcinoid syndrome, proliferative diabetic retinopathy, rosacea, pancreatitis, gastrointestinal bleeding, pancreatic and intestinal fistulas, Graves-Basedow opthalmopathy, glaucoma, and/or corneal disease associated with vascularization, the method comprising subcutaneously implanting at least one dry implantable device comprising a preparation encased in a hydrophilic polymer, wherein the preparation comprises octreotide, and wherein the hydrophilic polymer but not the preparation further comprises a release agent having a molecular weight of at least 1000, e.g., Vitamin E TPGS. In a particular embodiment, the preparation comprises about 40 mg to about 120 mg of octreotide acetate. In a particular embodiment, two implantable devices are implanted subcutaneously. In a particular embodiment, the implantable device remains implanted in a patient for a continuous time period ranging from about six months to about two years. In a particular embodiment, the implantable device remains implanted in the patient for a continuous time period ranging from about six months to about one year. In a particular embodiment, the implantable device is sterilized by irradiation.

In particular embodiments, the formulations and methods are used to treat, for example, severe diarrhea, watery diarrhea, flushing episodes and/or asthma.

One embodiment is directed to a kit comprising any of the formulations described herein. The kit can further comprise materials and instructions necessary for the implantation and use of the formulation.

DETAILED DESCRIPTION

Figure 1:
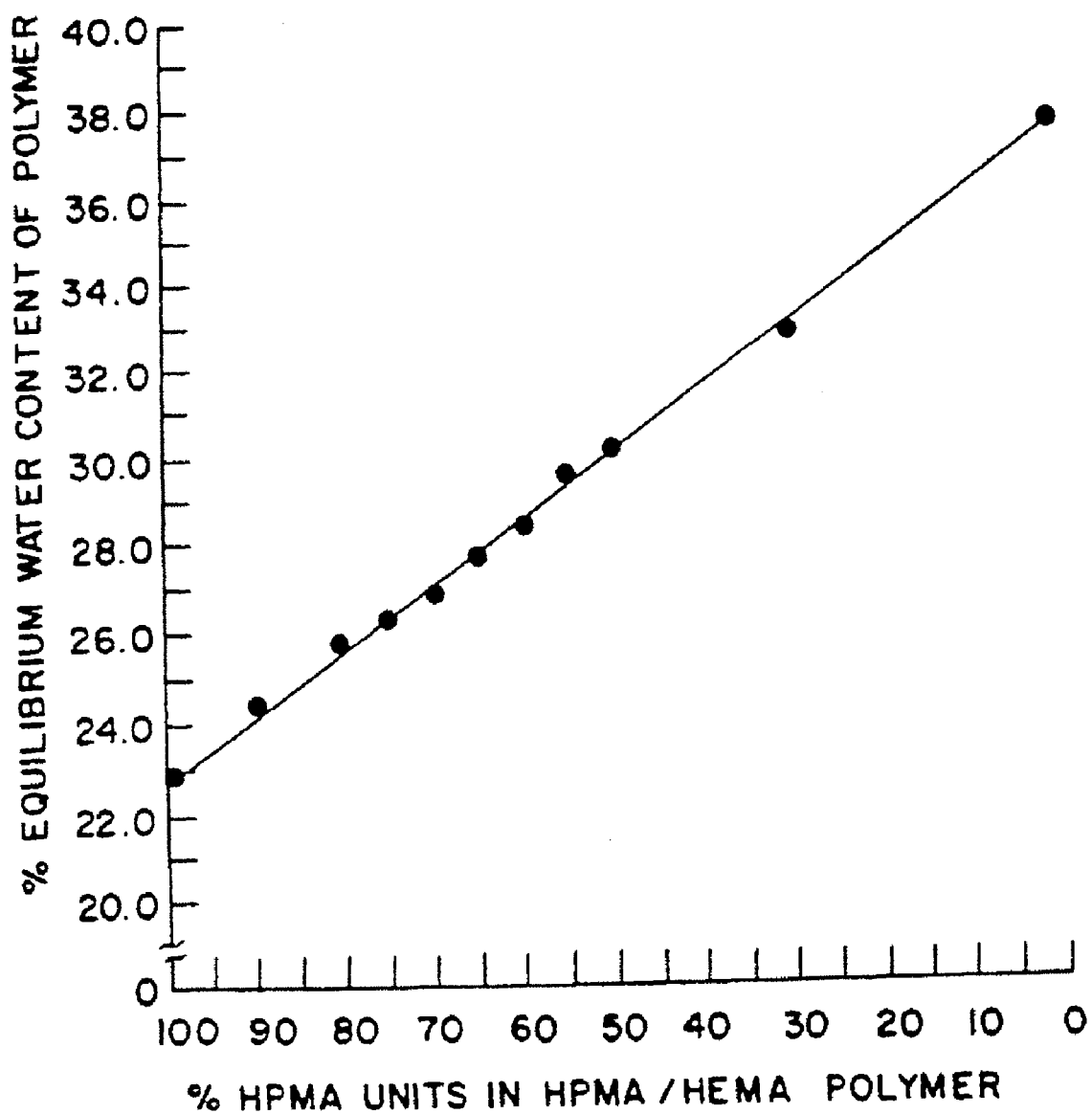
FIG. 1 is a graph showing the linear relationship between the equilibrium water content (EWC) vs. the weight percent content of hydroxypropyl methacrylate (HPMA) units in cross-linked HEMA/HPMA polymers at their maximum state of hydration.

Before the present compositions and methods are described, it is to be understood that they are not limited to the particular molecules, compositions, methodologies or protocols described, as these may vary. It is also to be understood that the terminology used in the description is for the purpose of describing the particular versions or embodiments only, and is not intended to limit the scope of the present invention, which will be limited only by the appended claims. The terms used herein have meanings recognized and known to those of skill in the art, however, for convenience and completeness, particular terms and their meanings are set forth below.

The singular forms "a", "an", and "the" include plural reference unless the context clearly dictates otherwise. Unless defined otherwise, all technical and scientific terms used herein have the same meanings as commonly understood by one of ordinary skill in the art. Although any methods and materials similar or equivalent to those described herein can be used in the practice or testing of embodiments described herein, the preferred methods, devices, and materials are now described. All publications mentioned herein are incorporated by reference to the extent they support the present invention. Nothing herein is to be construed as an admission that the invention is not entitled to antedate such disclosure by virtue of prior invention.

As used herein, the term "about" means plus or minus 10% of the numerical value of the number with which it is being used. For example, about 50% means in the range of 40%-60%.

"Controlled-release formulation" refers to a formulation designed to consistently release a predetermined, therapeutically effective amount of drug or other active agent such as a polypeptide or a synthetic compound over an extended period of time, with the result being a reduction in the number of treatments necessary to achieve the desired therapeutic effect. As described herein, a controlled formulation decreases the number of treatments necessary to achieve the desired effect in terms of decreased growth hormone (GH) levels or decreased IGF-1 levels, or an improvement in symptoms associated with acromegaly, including but not limited to abnormal growth. The controlled-release formulations achieve a desired pharmacokinetic profile in a subject, preferably commencement of the release of the active agent substantially immediately after placement in a delivery environment, followed by consistent, sustained, preferably zero-order, substantially zero-order, or near-zero order release of the active agent.

As used herein, the term "controlled-release" includes the predetermined, consistent release of active agent from the dosage formulation at a rate such that a therapeutically beneficial blood level below toxic levels of the active agent is maintained over a period, for example, of at least about two months, about six months or more (e.g., up to about two years).

The terms "patient" and "subject" mean all animals including humans. Examples of patients or subjects include humans, cows, dogs, cats, goats, sheep and pigs.

The term "pharmaceutically acceptable salts, esters, amides, and prodrugs" as used herein refers to those carboxylate salts, amino acid addition salts, esters, amides, and prodrugs of the compounds of the present invention that are, within the scope of sound medical judgment, suitable for use in contact with the tissues of patients without undue toxicity, irritation, allergic response and the like. Their use is commensurate with a reasonable benefit/risk ratio, and is effective for their intended use. Zwitterionic forms, where possible, can also be used. The compounds described herein can exist, for example, in unsolvated and solvated forms with pharmaceutically acceptable solvents such as, for example, water, ethanol and the like. In general, the solvated forms are considered equivalent to the unsolvated forms for the purposes of the present invention.

The term "prodrug" refers to compounds that are rapidly transformed in vivo to yield the parent compounds of the above formula, for example, by hydrolysis in blood. A discussion is provided in T. Higuchi and V. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are incorporated herein by reference in their entireties.

The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the acetate, hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate and laurylsulphonate salts, and the like. These can include cations based on the alkali and alkaline earth metals, such as sodium, lithium, potassium, calcium, magnesium, and the like, as well as non-toxic ammonium, tetramethylammonium, tetraethylammonium, methylamine, dimethylamine, trimethylamine, triethylamine, ethylamine and the like (See, for example, S. M. Barge et al., "Pharmaceutical Salts," J. Pharm. Sci., 1977, 66:1-19, which is incorporated herein by reference in its entirety).

"Treatment" refers to the administration of medicine or the performance of medical procedures with respect to a patient, either for prophylaxis (prevention) or to cure the infirmity or malady in the instance where the patient is afflicted.

A "therapeutically effective amount" is an amount sufficient to decrease, prevent or ameliorate the symptoms associated with a medical condition. In the context of hormonal therapy it can also mean an amount sufficient to normalize body functions or hormone levels in disease or disorders. A therapeutically effective amount of a controlled release formulation of octreotide, for example, is a predetermined amount calculated to achieve the desired effect, e.g., to effectively decrease GH or IGF-1 levels in a patient.

The present invention can be utilized to treat a variety of hormonal disorders, including, for example, acromegaly and gigantism, or other diseases or disorders that are effectively treated with, for example, octreotide. Acromegaly is characterized by a number of clinical features including enlargement of the hands and feet, facial changes including frontal bossing, enlarged mandible and increased dental spacing, arthralgias, diaphoresis, sleep apnea, hypertension, diabetes mellitus and hypertrophic cardiomyopathy. Tumors that cause acromegaly frequently cause local anatomic compression, resulting in, for example, visual field deficits, headaches, hypopituitarism, and cranial nerve palsies. There is a two- to five-fold increase in the mortality rate in acromegalic patients largely due to cardiovascular and cerebrovascular disease. There is also an increased rate of malignancy associated with acromegaly, with colon cancer the best characterized.

Octreotide is an octapeptide with the following amino acid sequence: L-cysteinamide, D-phenylalanyl-L-eysteiny-L-phenylalanyl-D-tryptophyl-L-lysyl-L-threonyl-N-[2-hydroxy-1-(hydroxymethyl)propyl]-,cyclic(2→7)-disulfide; [R—(R*,R*)]. The structure of octreotide is shown below.

stances, e.g., inorganic salts or hydroxides such as, for example, Ca, Zn and acetate salts and/or addition of polymeric organic substances.

Embodiments provide a drug delivery device that can achieve the following objectives: a controlled-release rate (zero- or substantially zero-order release rate) to maximize therapeutic effects and minimize unwanted side effects; a convenient way to retrieve the device if it is necessary to end the treatment; and an increase in bioavailability with less variation in absorption and no first pass metabolism.

The controlled-release pharmaceutical composition comprising octreotide acetate can be part of a controlled-release hydrogel device or hydrophilic polymer device. A composi-

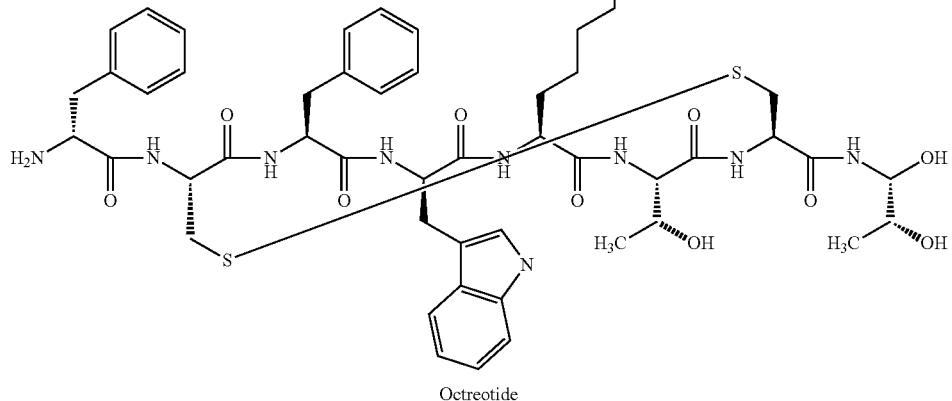

Octreotide

Octreotide inhibits GH, glucagon and insulin. It also suppresses LH response to GnRH, inhibits release of gastrin, decreases splanchnic blood flow, and inhibits the release of serotonin, secretin, motilin, vasoactive intestinal peptide, and pancreatic polypeptide. Octreotide also inhibits TSH (thyroid stimulating hormone). As a consequence, octreotide can be used to treat a number of conditions and symptoms, including, for example, acromegaly, diabetes, and severe diarrhea and flushing episodes associated with carcinoid tumors, VIPomas (Vasoactive Intestinal Peptide Secreting Adenomas), and neuroendocrine tumors, in particular, watery diarrhea associated with VIPomas, and can, in addition, be useful in treating symptoms associated with chemotherapy and AIDS. Octreotide is also useful in the treatment of a number of other conditions, such as, for example, proliferative diabetic retinopathy (Palii, S. et al., Expert Opin. Investig. Drugs, 16:73-82, 2007), rosacea (Pierard-Franchimont, C. et al., Dermatology, 206:249-251, 2003), pancreatitis, gastrointestinal bleeding, pancreatic and intestinal fistulas, Graves-Basedow opthalmopathy, glaucoma, and corneal disease associated with vasularization (Pawlikowski, M. and Melen-Mucha, G., Neuro. Endocrinol. Lett., 24:21-27, 2003).

The chemical formula is $C_{49}H_{66}N_{10}O_{10}S_2$ and its molecular weight is 1019.3 Da. Its therapeutic category is gastric anti-secretory agent. The octreotide of the present invention can exist in, for example, a free form, a salt form or in the form of complexes thereof. Acid addition salts can be formed with, for example, organic acids, polymeric acids and inorganic acids. Acid addition salts include, for example, the hydrochloride and acetates. Complexes are formed, for example, from octreotide upon addition of inorganic subtion of the present invention is capable of providing, upon administration to a patient, a release profile of octreotide extending over at least about two months, preferably at least about six months or more, e.g., up to about one year, or up to about two years. Octreotide can be contained within the hydrogel, for example, wherein the formulation releases a therapeutically effective amount of octreotide over an extended period of time. The hydrogel can comprise a hydrophilic polymer such as, for example, methacrylate-based polymers, polyurethane-based polymers and combinations thereof. A therapeutically effective amount is an amount of octreotide, preferably octreotide acetate, that, when administered to a patient or subject, ameliorates one or more symptoms of acromegaly. The formulation can further include pharmaceutically acceptable excipients.

When the compositions of the present invention are administered to a patient, the release of octreotide, measured, for example, as the concentration of octreotide in the patient's plasma over time (release profile), can extend over a period of at least about two months, about six months, up to about one year, at least about 12 months or one year, and/or up to about two years. The compositions provide a mean plasma concentration at steady state of octreotide in a human patient of from about 0.1 to about 9 ng/mL, about 0.5 ng/mL to about 1 ng/mL, about 1 to about 2 ng/mL, about 0.5 ng/mL to about 2 ng/mL, about 1.2 to about 1.6 ng/mL, or about 0.8 ng/mL to about 1.8 ng/mL. Steady state is the point at which the amount of drug administered over a dosing interval equals the amount of drug being eliminated over that same period.

The hydrophilic implant comprising the octreotide formulation can be formed from a xerogel such that it readily absorbs water. In a hydrated state, the xerogel is referred to as a hydrogel. In either form, hydrated or unhydrated, it is biocompatible and non-toxic to the host and non-biodegradable. It is water-swellable and water-insoluble. When the hydrogel attains its maximum level of hydration, the water content of the hydrogel is referred to as "equilibrium water content" (EWC). The percent water content of the hydrogel (any state of hydration) is determined as follows:

$$\frac{\text{weight of hydrogel} - \text{weight of dry polymer (xerogel)}}{\text{weight of hydrogel}} \times 100$$

The hydrogel can be a homogeneous homopolymer or copolymer having a predetermined EWC value formed by the polymerization of a mixture of ethylenically unsaturated monomer A and ethylenically unsaturated monomer B, for example, 2-hydroxyethyl methacrylate (HEMA) and hydroxypropyl methacrylate (HPMA). The predetermined EWC can be calculated by determining the EWC values of the hydrogel homopolymer of hydrophilic monomer A (homopolymer A) and the hydrogel homopolymer of hydrophilic monomer B (homopolymer B); determining the relationship of the EWC values of the homogeneous copolymers AB versus the chemical composition of said copolymers AB; selecting the targeted EWC value and determining the chemical composition of copolymer AB having the targeted EWC value; forming a polymerizable mixture of monomer A and monomer B in amounts sufficient to yield copolymer AB having the targeted EWC value; and effect the polymerization reaction to yield copolymer AB characterized by the targeted EWC value.

As used herein, "copolymer AB" or "copolymer AB consisting essentially of monomer A units and monomer B units" means that the addition copolymerization of monomer A and monomer B has been effected through the polymerizable ethylenic bond of the monomers. By way of illustration, if monomer A is 2-hydroxyethyl methacrylate and monomer B is N-methylacrylamide, copolymer AB contains recurring monomer A units and recurring monomer B units.

Unless the context indicates otherwise, the term "copolymer" includes polymers made by polymerizing a mixture of at least two ethylenically unsaturated monomers.

As used herein, "HEMA unit(s)" refer to a structure recurring in the polymer obtained by polymerizing hydrophilic material containing 2-hydroxyethyl methacrylate ("HEMA"). By the term "HEMA unit(s)" is meant the structure:

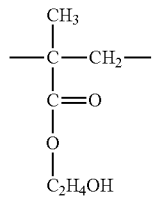

As used herein, "HPMA unit(s)" refers to a structure obtained by polymerizing hydrophilic material containing hydroxypropyl methacrylate ("HPMA"). By the term "HPMA unit(s)" is meant the structure:

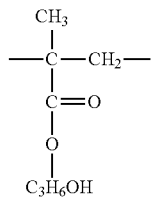

Liquid polymerizable material useful in the hydrophilic products include a wide variety of polymerizable hydrophilic, ethylenically unsaturated compounds, in particular, hydrophilic monomers such as, for example, the monoester of an acrylic acid or methacrylic acid with a polyhydroxy compound having an esterifiable hydroxyl group and at least one additional hydroxyl group such as, for example, the monoalkylene and polyalkylene polyols of methacrylic acid and acrylic acid, e.g., 2-hydroxyethyl methacrylate and acrylate, diethylene glycol methacrylate and acrylate, propylene glycol methacrylate and acrylate, dipropylene glycol methacrylate and acrylate, glycidyl methacrylate and acrylate, glyceryl methacrylate and acrylate, and the like; the 2-alkenamides, e.g., acrylamide, methacrylamide, and the like; the N-alkyl and N,N-dialkyl substituted acrylamides and methacrylamides such as N-methylmethacrylamide, N,N-dimethylmethacrylamide, and the like; N-vinylpyrrolidone; the alkyl-substituted N-vinylpyrrolidones, e.g., methyl substituted N-vinylpyrrolidone; N-vinylcaprolactam; the alkyl-substituted N-vinylcaprolactam, e.g., N-vinyl-2-methylcaprolactam, N-vinyl-3,5-dimethylcaprolactam, and the like. Acrylic and methacrylic acid can also be useful in these formulations.

Mixtures of hydrophilic monomers are employed in the polymerization reaction. The type and proportion of monomers are selected to yield a homogeneous polymer, preferably a crosslinked homogeneous polymer, which upon hydration possesses the desired EWC value for the contemplated application or use. This value can be predetermined by preparing a series of copolymers using different monomer ratios, e.g., mixtures of HEMA and HPMA of varying ratios, ascertaining the EWC values of the copolymers, and plotting the relationship of % HPMA (or % HEMA) units in the HPMA/HEMA copolymers versus weight percent EWC of the copolymers (FIG. 1).

In some instances the polymerization of certain hydrophilic monomeric mixtures results in homogeneous hydrophilic copolymers that dissolve, to a varying extent, in an aqueous medium. In such cases, a small amount, e.g., up to three percent, of a copolymerizable polyethylenically unsaturated crosslinking agent, can be included in the monomeric mixture to obtain homogeneous crosslinked copolymers that are water-insoluble as well as water-swellable. Slightly crosslinked homopolymers of HEMA can have an EWC value of, for example, about 38%. Crosslinked copolymers of HEMA and HPMA have EWC values below about 38%. On the other hand, crosslinked copolymers of HEMA and acrylamide exhibit EWC values above 38% (w/v), e.g., upwards to approximately 75%, and higher. Therefore, depending on the useful or effective elution rate of the active compound, e.g., drug, that is required of a hydrogel delivery system for a particular application, one skilled in the art, by following the teachings disclosed herein, can tailor copolymer hydrogel membranes to elute the drug at a desired rate. Copolymers can contain, for example, about 15% to about 70% (weight) of HEMA units and from about 85 to 30% (weight) of units of a second ethylenic monomer and possess predetermined EWC values in the range of from about 20% to about 75%, preferably about 25%. Homogenous copolymers can include those made from hydrophilic monomeric mixtures containing from about 60% HPMA (weight), and from about 20% HEMA (weight). For example, homogenous copolymers can include those made from hydrophilic monomeric mixtures containing about 60% HPMA (weight) and about 40% HEMA (weight), or containing about 80% HPMA (weight) and about 20% HEMA (weight). In further embodiments, the mixture can further contain a small amount of a polyethylenically unsaturated crosslinking agent, e.g., trimethylolpropane trimethacrylate ("TMPTMA").

Some embodiments include homogeneous hydrophilic copolymers with a homogeneous polymer structure formed by the polymerization of a mixture of hydrophilic monomers; and the drug delivery device that utilizes the homogeneous polymer cartridges in the delivery system. The polymerization of a mixture of hydrophilic monomers and hydrophobic monomers yields heterogeneous polymers. Where hydrophobic segments are present in the polymer, the interfacial free energy increases, thus enhancing protein adsorption and mineralization after implantation in an animal. Hydrogels of poly HEMA, for example, were measured to have interfacial free energy close to zero. According to the interfacial free energy interpretation, hydrogels of strictly hydrophilic components are biocompatible with body tissue. Slightly crosslinked poly HEMA is a homogeneous, hydrophilic "homopolymer" (disregarding the relatively small quantities of polymerized crosslinking agent therein) of relatively fixed characteristics or values. Techniques for altering the "homopolymer" poly HEMA to impart to it additional characteristics or properties are difficult, time-consuming, and oftentimes result in erratic property behavior. On the other hand, mixtures of HEMA with varying quantities of other polymerizable hydrophilic comonomer(s) can be polymerized to give predictable homogeneous hydrophilic copolymers having (predetermined) tailor made properties.

Useful crosslinking agents that can be included in the polymerizable reaction medium include, for example, the polyethylenically unsaturated compounds having at least two polymerizable ethylenic sites, such as the di-, tri- and tetra-ethylenically unsaturated compounds, in particular, the tri-unsaturated crosslinking agents with/without the di-unsaturated crosslinking compounds, for example, divinylbenzene, ethylene glycol dimethacrylate and diacrylate, propylene glycol dimethacrylate and diacrylate; and the di-, tri- and tetra-acrylate or methacrylate esters of the following polyols: triethanolamine, glycerol, pentaerythritol, 1,1,1 trimethylolpropane and others.

The polymerization reaction can be carried out in bulk or with an inert solvent. Suitable solvents include, for example, water; organic solvents (e.g., water-soluble lower aliphatic monohydric alcohols as well as polyhydric alcohols, e.g., glycol, glycerine, dioxane, etc.; and mixtures thereof).

Compounds useful in the catalysis of the polymerizable ethylenically unsaturated compounds include the free radical compounds and/or initiators of the type commonly used in vinyl polymerization such as the organic peroxides, percarbonates, hydrogen peroxides, and alkali metal sulfates. Illustrative examples include, but are not limited to, cumene hydroperoxide, t-butyl hydroperoxide, benzoyl peroxide, bis (4-t-butylcyclohexyl)peroxydicarbonate, hydrogen peroxide, 2,4-dichlorobenzoyl peroxide, acetyl peroxide, di-n-propyl peroxydicarbonate, di-t-butyl peroxide, di-sec-butyl peroxydicarbonate, ammonium sulfate, potassium sulfate, and sodium sulfate. In one embodiment, the catalyst is effective at a moderately low temperature such as, for example, at about 20-80° C. (e.g., tert-butyl peroctoate, benzoyl peroxide, and di(secbutyl) peroxydicarbonate).

A conventional redox polymerization catalyst can also be employed. Polymerization of the ethylenic compounds can be effected, for example, using radiation, e.g., ultraviolet, X-ray, gamma radiation, microwave or other known forms of radiation. An example of a catalyst for ultraviolet cure is benzoin methyl ether. Catalysts and/or initiators and/or radiation are employed in a catalytically effective amount to optimize the polymerization reaction.

Some embodiments focus on the application of polyurethane-based polymers, thermoplastics or thermosets, to the creation of implantable drug devices to deliver biologically active compounds at controlled rates for prolonged period of time. Polyurethane polymers can be made into cylindrical hollow tubes with one or two open ends through extrusion, (reaction) injection molding, compression molding or spin-casting (U.S. Pat. Nos. 5,266,325 and 5,292,515, herein incorporated by reference in their entireties), depending on the type of polyurethane used.

Thermoplastic polyurethane can be processed through extrusion, injection molding or compression molding. Thermoset polyurethane can be processed through reaction injection molding, compression molding or spin-casting. The dimensions of the cylindrical hollow tube are determinable and can be adjusted precisely.

Polyurethane-based polymers are synthesized from multifunctional polyols, isocyanates and chain extenders. The characteristics of each polyurethane can be attributed to its structure.

Thermoplastic polyurethanes are made of macrodiols, diisocyanates and difunctional chain extenders (U.S. Pat. Nos. 4,523,005 and 5,254,662, herein incorporated by reference in their entireties). Macrodiols make up the soft domains. Diisocyanates and chain extenders make up the hard domains. The hard domains serve as physical crosslinking sites for the polymers. Varying the ratio of these two domains can alter the physical characteristics of the polyurethanes.

Thermoset polyurethanes can be made of multifunctional (greater than difunctional) polyols and/or isocyanates and/or chain extenders (U.S. Pat. Nos. 4,386,039 and 4,131,604, herein incorporated by reference in their entireties). Thermoset polyurethanes can also be made by introducing unsaturated bonds in the polymer chains and appropriate cross-linkers and/or initiators to do the chemical crosslinking (U.S. Pat. No. 4,751,133, herein incorporated by reference in its entirety). By controlling the amounts of crosslinking sites and how they are distributed, the release rates of the actives can be controlled.

Different functional groups can be introduced into the polyurethane polymer chains through the modification of the backbones of polyols depending on the properties desired. Where the device is used for the delivery of water soluble drugs, hydrophilic pendant groups such as ionic, carboxyl, ether, and hydroxy groups are incorporated into the polyols to increase the hydrophilicity of the polymer (U.S. Pat. Nos. 4,743,673 and 5,354,835, herein incorporated by reference in their entireties). Where the device is used for the delivery of hydrophobic drugs, hydrophobic pendant groups such as alkyl, siloxane groups are incorporated into the polyols to increase the hydrophobicity of the polymer (U.S. Pat. No. 6,313,254, herein incorporated by reference in its entirety). The release rates of the actives can also be controlled by the hydrophilicity/hydrophobicity of the polyurethane polymers.

One or more release agents are optionally included in the polymer of the implantable drug delivery devices described herein. For those embodiments in which the cartridge is produced using a mold, for example, one or more release agents are optionally present in the polymer matrix of the cartridge to aid in removal of the cartridge from the mold.

Release agents in general are compounds capable of allowing effective release of a molded article from a mold. For the devices described herein, the release agent is typically combined with the polymerizable reaction medium prior to introducing the polymerizable material to a mold.

Release agents suitable for use in the implantable devices are safe for introduction into a patient, do not adversely react with the polymer of the molded article, for example, by causing weakening of the structure of the article, and optionally protect the polymer cartridge from adverse effects of sterilization. Without being bound by theory, it is believed that higher molecular weight release agents provide improved release characteristics over those provided by lower molecular weight release agents. Release agents accordingly can have a molecular weight (MW) in excess of about 1000. In other embodiments, the release agents have a MW in excess of about 1200, from about 1000 to about 2000, or between about 1200 and about 1800.

Suitable release agents include non-ionic surfactants. In some embodiments, for example, the release agent is Vitamin E TPGS. Vitamin E TPGS is an abbreviation for D-□-tocopheryl (Vitamin E) polyethylene glycol 1000 succinate. Non-ionic surfactants release agents provide excellent release properties and are non-reactive with the molded article while providing a safety profile that is suitable for implants. These release agents additionally can act as antioxidants or free radical scavengers and, therefore, prevent or reduce adverse effects on the molded article associated with sterilization of the molded article, especially sterilization methods that can generate free radicals, including irradiation methods. In particular embodiments, the release agent dissolves in a desired monomer mixture. A hydrophilic monomer material, such as, for example combinations of HEMA, HPMA and HBMA, can be used in combination with an amphiphilic release agent, such as, for example, Vitamin E TPGS, during the molding process.

Non-ionic surfactants are known in the art, and may generally consist of a polyethylene glycol hydrophilic tail and a lipophilic head. For Vitamin E TPGS, for example, the lipophilic head is tocopherol succinate and for Triton X-100 it is an isooctylphenyl group. Non-ionic surfactants can be characterized by several parameters, such as, for example, hydrophilic-lipophilic balance (HLB), which relates the size of the polyethylene glycol tail to the lipophilic head; critical micelle concentration (CMC), which is the concentration of surfactant at which micelles form; and MW, which describes the size of the hydrophilic and lipophilic portions relative to other surfactants with similar properties. Additionally, CMC is an indication of the surface activity of the surfactant, and a low CMC is indicative of a more stable micelle because of stronger binding forces. The Table below lists several surfactants and their physical properties.

| Name | ~MW | HLB | CMC (mM) |
| --- | --- | --- | --- |
| Triton X-100 | 625 | 13.5 | 0.2-0.9 |
| Vitamin E TPGS | 1513 | 13 | 0.1 |
| Triton X-114 | 537 | 12.4 | 0.2 |
| Brij 35 | 1200 | 16.9 | 0.05-0.1 |
| Tween 20 | 1228 | 16.7 | 0.06 |
| Tween 80 | 1310 | 15 | 0.012 |
| Sucrose monolaurate | 525 | ~8 | 0.2 |

Additional release agents for use in combination with the implantable devices include, but are not limited to, polyoxyethylene(2) stearyl ether, sorbitan monolaurate, polyoxyethylene(5)nonylphenyl ether, polyoxyetheylene(20)sorbitan trioleate, polyoxyethylene(10)isooctylphenyl ether, and the like, or combinations of these release agents.

In certain embodiments, the release agent is a polyoxyethylene ester of fatty acids or other hydrophobic compounds. These compounds are known in the art and include a polyoxyethylene tail and a saturated or unsaturated hydrophobic head. The hydrophobic moiety of various embodiments can include any aromatic group containing moiety or polycyclic aromatic moieties such as, for example, a phenol, a catechol, a resorcinol, a hydroquinone, a tocopherol, Vitamin E, and the like and can be isoprenoid or no-isoprenoid. The side chains associated with these aromatic moieties can be of any length and can additionally include any number of double bonds and/or substitutions. Non-ionic surfactants, for example, can include, but are not limited to, naturally occurring or commercially manufactured tocopherols including any isoform, racemate, or chemically modified derivative, such as, Vitamin E TPGS. Tocopherols can also include oxidation products of tocopherols, such as the oxidation products of □-tocopherol, tocopherol quinones, tocopherol hydroquinones, epoxytocopherols, and nitrotocopherols.

Small cylindrically shaped implants can contain within their core, octreotide, e.g., octreotide acetate, and optionally, a pharmaceutically acceptable carrier. The membrane thickness (between the interior and exterior surfaces) of the implant is substantially uniform, and serves as a rate-limiting barrier for the release of the contained agent. Such implants can be plasticized or hydrated and reshaped into other geometrically shaped articles for use in various medical applications.

In the manufacture of the implantable formulation, several factors can be considered. The release profile (delay time, release rate, and duration) is determined; the hydrophilic polymeric material is identified; and the diffusivity of the active agent through it (as a rate-limiting membrane) is measured. The hydration profile of the rate-limiting membrane for a given active agent may be readily determined by preparing a film of the selected polymer and subjecting it to a diffusion study, using a two compartment vertical glass cell, as is known in the art.

The diffusion coefficient and the water content at which diffusion begins (below which substantially no diffusion occurs—hereinafter "% Hd") are determined. A series of membranes is prepared from various polymers. The membranes are then hydrated to their capacity and their EWCs are measured. The fully hydrated membranes are placed in the two-compartment, vertical glass cells to measure and the diffusion of the macromolecular composition through the membrane materials at the various EWCs is plotted. The EWC of the most hydrated membrane through which no diffusion is detected (e.g., none of the active agent diffuses into the receptor cell) is the % Hd for the system being tested. This can be accomplished by plotting a curve of the permeability versus EWC.

The permeability results (diffusion coefficients) are obtained according to Fick's First Law of Diffusion, by use of the equation:

$$\frac{dQ}{dt} = \frac{APC_d}{1}$$

wherein dQ/dt is the flux through the membrane material (μg/hr); it is measured as the slope of the linear part of the curve of cumulative transport versus time; wherein A is the area of the membrane (cm2); wherein P is the membrane's permeability coefficient (cm2/hr), or DKd, wherein D is the diffusivity of the membrane (cm2/hr), and Kd is the partition coefficient for the membrane/donor solution; wherein 1 is the membrane thickness as measured at the end of the experiment (cm); and wherein Cd is the concentration of the donor solution (μg/cm 3).

The release delay profile can then be determined. Another series of polymeric membranes can be prepared, again varying the amounts of crosslinker and monomers. These membranes are then hydrated, but only partially, e.g., to a water content less than or equal to % Hd. The partially hydrated membranes are placed in two-compartment vertical glass cells to measure and plot the diffusion of the active compound through the membranes versus time. Buffer solutions for the donor and receptor cells can be selected to contact the partially hydrated membranes and further hydrate them at approximately the same rate at which they will hydrate in the delivery environment. The time between commencement of the diffusion study, i.e., addition of the active agent to the donor cell, and the detection of a pharmaceutically effective concentration of the active agent in the receptor cell is the release delay time for that combination of polymer and initial percent hydration.

To determine the physical dimensions of the cylindrically shaped device, the total amount of active agent to be delivered is determined. This is the product of the desired daily dosage and the duration of delivery. In preferred embodiments, the duration of delivery is at least about two months, at least about 6 months, or up to about two years. The desired daily dosage can be, for example, about 10 to about 1000 μg of octreotide per day, about 20 to about 800 μg of octreotide per day, about 75 to about 300 μg of octreotide per day, or about 30 to about 300 μg of octreotide per day.

The volume of the cylindrical reservoir (core) of a cylindrically shaped device is equal to $\Pi r_i^2 h$ wherein $r_i$ is the radius of the reservoir and h is its height. The formula for steady state release from a cylinder is:

$$[dQ/dt] = [2\Pi_h D K_d C_d]/[\ln(r_o/r_i)]$$

wherein $r_o$ is the outside radius of the cylindrical device; and wherein Cd is the concentration of drug in the donor solution, i.e., the carrier. Steady-state release is obtained when Cd is maintained at saturation. The thickness of the membrane needed for the desired sustained release is, therefore, $r_o - r_i$.

The amount of active agent employed depends not only on the desired daily dose but also on the number of days that dose level is to be maintained. While this amount can be calculated empirically, the actual dose delivered is a function of any interaction with materials and the carrier, if employed in the device.

Once the appropriate polyurethane polymer is chosen, the best method to fabricate the cylindrically shaped implants can be determined by one of skill in the art to achieve suitable delivery characteristics as described herein.

For thermoplastic polyurethanes, precision extrusion and injection molding can be used to produce two open-ended hollow tubes with consistent physical dimensions. The reservoir can be loaded freely with appropriate formulations containing active agents ("actives") and carriers or filled with pre-fabricated pellets to maximize the loading of the actives. To seal the two open ends, two pre-fabricated end plugs can be used. The sealing step can be accomplished through the application of heat or solvent or any other means to seal the ends, preferably permanently.

For thermoset polyurethanes, precision reaction injection molding or spin casting can be used, depending on the curing mechanism. Reaction injection molding is used if the curing mechanism is carried out through heat and spin casting is used if the curing mechanism is carried out through light and/or heat. Hollow tubes with one open end can be made, for example, by spin casting. Hollow tubes with two open ends, for example, can be made by reaction injection molding. The reservoir can be loaded in the same way as the thermoplastic polyurethanes.

An appropriate light-initiated and/or heat-initiated thermoset polyurethane formulation can be used to fill the open. This is cured with light and/or heat, thereby sealing the previously open end. A pre-fabricated end plug can also be used to seal the open end by applying an appropriate light-initiated and/or heat-initiated thermoset polyurethane formulation on to the interface between the pre-fabricated end plug and the open end; the plug can be cured with the light and/or heat or any other means to seal the ends, preferably permanently. The solid active agent and optional carriers can be compressed into pellet form to maximize the loading of the actives.

The external surface area of the implant, e.g., the external surface area of the polymer cartridge or hollow tube, can vary. In some embodiments, the surface area of the polymer cartridge can have a surface area of from about 350 mm2 to about 1500 mm2. Hydrated implants and xerogel (e.g., non-hydrated, or dry) implants have different dimensions and, therefore, different surface areas. In some embodiments, the release agents are used in the preparation of larger implant devices. A xerogel, non-hydrated, or dry implant, for example can have a surface area of about 350 mm2 or greater. Alternatively, a xerogel, non-hydrated, or dry implant can have a surface area of from about 350 mm2 to about 1500 mm2, or from about 350 mm2 to about 600 mm2. The dry implant, for example, can have a surface area from 378 mm2 to 660 mm2. Additionally, a hydrated implant can have a surface area of about 500 mm2 or greater. The hydrated implant alternatively can have a surface area of from about 600 mm2 to about 1500 mm2, or from about 600 mm2 to about 800 mm2. As used herein, the term "hydrated implant" refers to implants having a water content of 5% (wt), or greater, and are thus soft and flexible. As used herein, "dry implant" refers to implants that are rigid and inflexible, having a water content less than 5% (wt), in some embodiments, and less than 1% (wt), in other embodiments.

The implantable devices can be inserted subcutaneously in a human or other animal by any suitable means known in the art, e.g., by perforation (for subcutaneous implantation) or by other means, e.g., open surgery (U.S. Pat. No. 5,266,325, which discloses examples of methods and devices that can be used to implant the devices; the entire contents of U.S. Pat. No. 5,266,325 are herein incorporated by reference). The implantable device can be inserted subcutaneously in the human or animal by perforation, for example. In addition, more than one device can be implanted into the human or animal at the same time, e.g., substantially simultaneously, so that multiple devices are present as implants in the human or animal. Thus, in some embodiments, at least one device is implanted into the human or animal. Alternatively, multiple devices can be implanted sequentially, so that only one device is present in the human or animal at any one time.

Prior to implantation, the implantable formulations can be optionally hydrated or "primed" for a predetermined period of time. Priming can enable the active ingredient to begin to infiltrate and saturate the walls of the hydrogel and potentially begin to leach out of the hydrogel prior to implantation depending upon the amount of time the implant is primed. A primed implant begins to release active ingredient substantially upon implantation, and can result in a peak release of the drug shortly after implantation. In contrast, little to no priming can result in substantially no release of the active ingredient upon implantation for a period of time until the implant becomes hydrated and the active ingredient begins to be released. These priming characteristics depend on the specific formulations being used.

Depending upon the types of active ingredient, hydrophilic or hydrophobic, the appropriate conditioning and priming media are chosen. Water-based media are preferred for hydrophilic actives and oil-based media are preferred for hydrophobic actives. Alternatively, certain implants do not need to be primed prior to implantation. In some instances, priming improves delivery of the active agent in a controlled fashion, but in other instances, priming prior to implantation in a subject does not affect delivery in a way to justify the added time and hassle required for priming the implant.

The hydrating liquid useful in the practice of the invention is typically a liquid simulating the environment in which the active compound will be released, e.g., body fluid, sterile water, tear fluid, physiological saline solution, phosphate buffer solution and the like. While liquids other than water are useful as the hydrating liquid, the degree to which a hydrophilic membrane is hydrated is referred to as its "water content."

The priming and conditioning of the drug delivery devices involves the loading of the actives (drug) into the polymer that surrounds the reservoir, and thus prevent loss of the active before the actual use of the implant. The conditions used for the conditioning and priming step depend on the active agent, the temperature and the medium in which they are carried out. The conditions for the conditioning and priming can be the same in some instances.

The conditioning and priming step in the process of the preparation of the drug delivery devices is performed to obtain a determined rate of release of a specific drug. The conditioning and priming step of the implant containing a hydrophilic drug can be carried out in an aqueous medium, e.g., in a saline solution. For hydrophobic drugs, the medium can be a plasma-like medium, including, for example, cyclodextrin. The conditioning and priming steps are carried out by controlling three specific factors, namely the temperature, the medium and the period of time.

A person skilled in the art would understand that the conditioning and priming step of the drug delivery device is affected by the medium in which the device is placed.

The temperature used to condition and prime the drug delivery device can vary across a wide range of temperatures, but, in some embodiments, 37° C., is used.

The time period used for the conditioning and priming of the drug delivery devices can vary from about an hour, about 1 to about 12 hours, about 2 to about 24 hours, about a single day, or up to several weeks, e.g., 6 weeks, depending on the release rate desired for the specific implant or drug.

A person skilled in the art will understand the steps of conditioning and priming the implants, where appropriate or necessary, is to optimize the rate of release of the drug contained within the implant. As such, a shorter time period spent on the conditioning and the priming of a drug delivery device can result, for example, in a lower rate of release of the drug compared to a similar drug delivery device that has undergone a longer conditioning and priming step. Without priming, however, it was unexpectedly found that effective release occurred over a longer period of time (e.g., 28 weeks and beyond), and lower serum concentrations of the active ingredient were found to have ameliorative effects.

The temperature in the conditioning and priming step can also affect the rate of release in that a lower temperature results in a lower rate of release of the drug contained in the drug delivery device when compared to a similar drug delivery device that has undergone a treatment at a higher temperature. Similarly, in the case of aqueous solutions, e.g., saline solutions, the sodium chloride content of the solution determines the release rate for the drug delivery device. More specifically, a lower content of sodium chloride can result in a higher rate of release of drug when compared to a drug delivery device that has undergone a conditioning and priming step where the sodium chloride content was higher.

To identify the location of the implant, radiopaque material can be incorporated into the delivery device by inserting it into the reservoir or by making it into end plug to be used to seal the cartridge.

The formulation of the present invention can contain a pharmaceutically acceptable carrier that can include, for example, suspending media, solvents, aqueous systems and solid substrates or matrices. Suspending media and solvents useful as the carrier include, for example, oils such as, for example, silicone oil (particularly medical grade), corn oil, castor oil, peanut oil and sesame oil; condensation products of castor oil and ethylene oxide; liquid glyceryl triesters of a lower molecular weight fatty acid; lower alkanols; glycols; and polyalkylene glycols. The aqueous systems include, for example, sterile water, saline, dextrose, dextrose in water or saline, and the like. The presence of electrolytes in the aqueous systems may tend to lower the solubility of the macromolecular drug in them. The solid substrates or matrices include, for example, starch, gelatin, sugars (e.g., glucose), natural gums (e.g., acacia, sodium alginate), modified celluloses (e.g., hydroxypropyl cellulose, hydroxyethyl cellulose, methyl cellulose, sodium carboxymethyl cellulose), modified starch, crosslinked polyvinyl pyrrolidone, and the like. In some embodiments, the pharmaceutical formulation further comprises about 2% to about 20% (e.g., about 10%) hydroxypropylcellulose.

The carrier can also contain adjuvants; preserving, stabilizing, wetting and emulsifying agents and the like; or other excipients, such as, for example, glidants, dissolution agents, surfactants, diluents, binders, disintegrants, and/or lubricants. For some embodiments, for example, the carrier contains an excipient such as magnesium stearate, stearic acid, vegetable stearin, talc or silica.

In some embodiments, the pharmaceutical formulation comprises a formulation of octreotide acetate within a mixture of HEMA and HPMA copolymer, e.g., about 20% HEMA and about 80% HPMA. The pharmaceutical formulation can comprise, for example, about 20 to about 150 milligrams of octreotide, about 40 to about 120 milligrams, or about 40 to about 90 milligrams of octreotide. In some embodiments, for example, the pharmaceutical formulation comprises about 50 milligrams of octreotide, or about 85 milligrams of octreotide. The formulation can further comprise between about 2% to about 20% excipients. The formulation can also contain about 10% hydroxypropylcellulose and/or about 2% magnesium stearate.

A pharmaceutical formulation can comprise, for example, a formulation of about 83 mg of octreotide within a mixture of HEMA and HPMA copolymer, e.g., about 40% HEMA and about 60% HPMA. In a further embodiment, the formulation further comprises about 10% hydroxypropylcellulose and 2% magnesium stearate with the octreotide acetate.

A pharmaceutical formulation can also comprise a formulation of about 20 milligrams to about 150 milligrams, about 40 to about 120 milligrams, or about 40 milligrams to about 90 milligrams, of octreotide in a polyurethane-based polymer.

A method of treating a disease or disorder, or alleviating its symptoms, is provided, e.g., a method of treating a disease associated with a hormonal disorder, such as a GH or IGF-1 hormone disorder or its symptoms. The method can include administering octreotide to a subject in need thereof such that the dose amounts of octreotide received by the subject result in octreotide serum levels ranging from about 0.8 ng/mL to about 1.8 ng/mL, or in which the dose amounts of octreotide received by the subject result in octreotide serum levels having a Cmax falling below about 1.3 ng/mL, or result in octreotide serum levels having a Cmax falling below about 1.0 ng/mL. In some embodiments, at least one implantable device described herein is implanted into a subject in need thereof, and the device delivers octreotide to the subject in a substantially zero-order release profile and over an extended period of time, e.g., no less than six months. The device can be implanted subcutaneously and in a hydrated or dry state. The device can also comprise an octreotide-containing preparation encased in a hydrophilic polymer, which can comprise one or more polyurethane-based polymers, or one or more methacrylate-based polymers. In some embodiments, a delay is observed in the release of octreotide, which lasts about one or more days from the date of implantation.

In some embodiments, a method is provided for delivering octreotide to a subject in need thereof in a substantially zero-order release profile and over an extended period of time, but no less than about six months, the method comprising implanting in a subject in need thereof, subcutaneously and in a dry state, at least one implantable device comprising an octreotide-containing preparation encased in a hydrophilic polymer, such that the subject receives, on a daily basis over a period of at least about six months, dose amounts of octreotide, which are effective to treat a disorder or alleviate its symptoms.

The methods can also include administering octreotide, thereby, for example, decreasing GH and/or IGF-1, and maintaining a plasma concentration at steady state of octreotide between about 0.1 ng/mL and about 9 ng/mL over an extended period of time, e.g., at least about two months, about six months, up to about one year, at least for a period of about 12 months or one year, and/or up to about two years. The plasma concentration at steady state of octreotide can be maintained, for example, between about 1 ng/mL and about 4 ng/mL, about 1 ng/mL and about 2 ng/mL, or about 1.2 ng/mL to about 1.6 ng/mL, over an extended period of time, e.g., at least about two months, and about six months, and up to about two years. Hormonal disorders include, for example, acromegaly.

The invention is further directed to methods of treating acromegaly comprising administering at least one implant, two implants, or two or more implants as described herein. Each implant administered can contain between about 20 to about 150 milligrams of octreotide, about 40 to about 90 milligrams of octreotide, or about 50 milligrams of octreotide, and release a therapeutically effective amount of octreotide over a period of at least two months, about six months, or up to about two years.

The invention is further directed to methods of treating symptoms associated with carcinoid tumors, VIPomas, and neuroendocrine tumors, such as, for example, severe diarrhea, watery diarrhea, and flushing, and to methods of treating carcinoid syndrome. The invention is further directed to treating symptoms associated with chemotherapy and AIDS.

Carcinoid tumors usually appear in the appendix, bronchial tubes, colon, or small intestine and secrete chemicals which cause the dilation of blood vessels—such as serotonin. Vasodilation may be responsible for the symptoms usually observed with carcinoid tumors, such as diarrhea, flushing, and asthma. Depending on the hormones and biochemicals secreted by carcinoid tumors, a number of symptoms may present—collectively known as Carcinoid Syndrome. Biochemically, people with carcinoid tumors tend to produce more serotonin, using the amino acid tryptophan as a base. Serotonin is further broken down in the body to product 5-hydroxyindole acetic acid (5-HIAA), which is seen in the urine of such patients.

The invention is also directed to methods of treating watery diarrhea, severe diarrhea and flushing episodes associated with carcinoid tumors by administering an implantable formulation of octreotide, which releases a therapeutically effective amount of octreotide over at least about two months, about six months and up to about two years.

The invention is also directed to a method of treating a condition selected from the group consisting of proliferative diabetic retinopathy, rosacea, pancreatitis, gastrointestinal bleeding, pancreatic and intestinal fistulas, Graves-Basedow opthalmopathy, glaucoma, and corneal disease associated with vascularization, the method comprising implanting subcutaneously in a dry state at least one implantable device comprising an octreotide-containing preparation encased in a hydrophilic polymer, the hydrophilic polymer but not the octreotide-containing preparation further comprising Vitamin E TPGS.

The formulations described herein exhibit a specific, desired release profile that maximizes the therapeutic effect while minimizing adverse side effects of the implant. The desired release profile can be described in terms of the maximum plasma concentration of the drug or active agent (Cmax) and the plasma concentration of the drug or active agent at steady state (Css). Administration of formulations, for example, can result in a subject's receiving dose amounts of octreotide that result in octreotide serum levels in the subject with a Cmax falling below about 1.3 ng/mL, or result in octreotide serum levels with a Cmax falling below about 1.0 ng/mL.

The present invention is also directed to therapeutic compositions of a hydrogel and octreotide, wherein, upon implantation, the octreotide is released at a rate that provides and/or maintains a Css of about 0.1 ng/mL to about 9 ng/mL, about 0.5 ng/mL to about 1 ng/mL, about 1 ng/mL and about 4 ng/mL, about 1 ng/mL to about 2 ng/mL, or about 1.2 ng/mL to about 1.6 ng/mL. A further embodiment is a therapeutic composition of a hydrogel and octreotide, wherein, upon implantation, the octreotide is released at a rate of from about 10 μg to about 1000 μg per day over an extended period of time, e.g., about 20 μg to about 800 μg, about 30 μg to about 800 μg, about 75 μg to about 300 μg per day or about 30 μg to about 300 μg per day. The octreotide can be released over a period of at least about two months, about six months, at least about 12 months or one year, or up to about two years. The hydrogel can comprise methacrylate-based polymers or polyurethane-based polymers.

Another embodiment is a controlled-release formulation comprising octreotide and a hydrophilic polymer (e.g., a controlled-release formulation comprising an octreotide-containing preparation encased in a hydrophilic polymer), wherein the controlled-release formulation is effective to permit release of the octreotide at a rate of about 30 μg to about 800 µg per day over at least about two months, about six months, about one year, at least 12 months or one year, or about two years in vitro. In some embodiments, delivery is about 100 µg to about 250 µg per day, or about 100 µg to about 130 µg per day. In a further embodiment, the hydrophilic polymer of the formulation permits release of octreotide at an average rate of about 100 µg per day in vitro. In some embodiments, the controlled-release formulation further comprises a release agent having a molecular weight (MW) of at least 1000. The hydrophilic polymer can be selected from polyurethane-based polymers and methacrylate-based polymers.

A further embodiment of the present invention is directed to a controlled-release formulation for implantation comprising an octreotide-containing preparation encased in a hydrophilic polymer such as, for example, polyurethane-based polymers and methacrylate-based polymers, wherein said controlled release formulation is effective to permit release of said octreotide at a rate of about 30 µg to about 800 µg per day over about six months in vivo, the hydrophilic polymer but not the octreotide-containing preparation further comprising a release agent having a molecular weight (MW) of at least 1000.

Yet a further embodiment of the present invention is a controlled-release formulation comprising octreotide for implantation, wherein the formulation comprises octreotide in a hydrophilic polymer effective to permit in vitro release of no more than about 20% of the octreotide from the formulation after about six weeks; and about 60% of the octreotide from the formulation after about six months.

The amount of a pharmaceutically acceptable octreotide (e.g., various salts, salvation states, or prodrugs thereof) included in the pharmaceutical composition of the present invention varies depending upon a variety of factors, including, for example, the specific octreotide used, the desired dosage level, the type and amount of hydrogel used, and the presence, types and amounts of additional materials included in the composition. The amount of octreotide, or a derivative thereof, in the formulation varies depending on the desired dose for efficient drug delivery, the molecular weight, and the activity of the compound. The actual amount of the used drug can depend on a patient's age, weight, sex, medical condition, disease or any other medical criteria. The actual drug amount is determined according to intended medical use by techniques known in the art. The pharmaceutical dosage formulated according to the invention can be administered, for example, about once every six months as determined by the attending physician.

Octreotide can be formulated in the implant or other pharmaceutical composition in amounts of about 20 milligrams to about 150 milligrams, e.g., about 40 to about 120 milligrams of octreotide, about 40 to about 90 milligrams of octreotide, or about 50 to about 85 milligrams. For adults, the daily dose for treatment of acromegaly is typically about 300 µg to about 600 µg of immediate release octreotide per day (100 µg or 200 µg Sandostatin®). The amount of octreotide in the composition can be selected, for example, to release from about 10 µg to about 1000 µg per day over an extended period of time, about 20 µg to about 800 µg per day, or about 30 µg to about 300 µg per day. Such release rates maintain desired therapeutic levels in a patient's blood at about 0.1 to about 9 ng/mL over an extended period of time.

The hydrogel device in which octreotide is contained provides a controlled-release of octreotide into the plasma of the patient. Hydrogels suitable for controlling the release rate of octreotide for use in the pharmaceutical compositions of the present invention include polymers of hydrophilic monomers, including, but not limited to HPMA, HEMA and the like. Such hydrogels are also capable of preventing degradation and loss of octreotide from the composition.

A pharmaceutical formulation can comprise octreotide acetate within a hydrophilic copolymer of 2-hydroxyethyl methacrylate and hydroxypropyl methacrylate. The copolymer of the pharmaceutical formulation can comprise, for example, about 20% HEMA and about 80% HPMA. The copolymer of the pharmaceutical formulation can alternatively comprise, for example, about 40% HEMA and about 60% HPMA.

The size, shape and surface area of the implant can be modified to increase or decrease the release rate of octreotide from the implant.

The pharmaceutical composition can include also auxiliary agents or excipients, for example, glidants, dissolution agents, surfactants, diluents, binders including low temperature melting binders, disintegrants and/or lubricants. Dissolution agents increase the dissolution rate of octreotide from the dosage formulation and can function by increasing the solubility of octreotide. Suitable dissolution agents include, for example, organic acids such as citric acid, fumaric acid, tartaric acid, succinic acid, ascorbic acid, acetic acid, malic acid, glutaric acid and adipic acid, which can be used alone or in combination. These agents can also be combined with salts of the acids, e.g., sodium citrate with citric acid, to produce a buffer system.

Other agents that can alter the pH of the microenvironment on dissolution and establishment of a therapeutically effective plasma concentration profile of octreotide include salts of inorganic acids and magnesium hydroxide. Other agents that can be used are surfactants and other solubilizing materials. Surfactants that are suitable for use in the pharmaceutical composition of the present invention include, for example, sodium lauryl sulfate, polyethylene stearates, polyethylene sorbitan fatty acid esters, polyoxyethylene castor oil derivatives, polyoxyethylene alkyl ethers, benzyl benzoate, cetrimide, cetyl alcohol, docusate sodium, glyceryl monooleate, glyceryl monostearate, glyceryl palmitostearate, lecithin, medium chain triglycerides, monoethanolamine, oleic acid, poloxamers, polyvinyl alcohol and sorbitan fatty acid esters.

Diluents that are suitable for use in the pharmaceutical compositions described herein include, for example, pharmaceutically acceptable inert fillers such as, for example, microcrystalline cellulose, lactose, sucrose, fructose, glucose dextrose, or other sugars, dibasic calcium phosphate, calcium sulfate, cellulose, ethylcellulose, cellulose derivatives, kaolin, mannitol, lactitol, maltitol, xylitol, sorbitol, or other sugar alcohols, dry starch, saccharides, dextrin, maltodextrin or other polysaccharides, inositol or mixtures thereof. The diluent can be a water-soluble diluent. Examples of diluents include, for example: microcrystalline cellulose such as Avicel PH112, Avicel PH101 and Avicel PH102 available from FMC Corporation; lactose such as lactose monohydrate, lactose anhydrous, and Pharmatose DCL 21; dibasic calcium phosphate such as Emcompress available from Penwest Pharmaceuticals; mannitol; starch; sorbitol; sucrose; and glucose. Diluents are carefully selected to match the specific composition with attention paid to the compression properties. The diluent can be used in an amount of about 2% to about 80% by weight, e.g., about 20% to about 50% by weight, of the controlled-release composition.

Glidants are used to improve the flow and compressibility of ingredients during processing. Suitable glidants include, for example, colloidal silicon dioxide, a sub-micron fumed silica that can be prepared, for example, by vapor-phase hydrolysis of a silicon compound such as, for example, silicon tetrachloride. Colloidal silicon dioxide is a sub-micron amorphous powder that is commercially available from a number of sources, including Cabot Corporation (under the trade name Cab-O-Sil®); Degussa, Inc. (under the trade name Aerosil®); and E.I. DuPont & Co. Colloidal silicon dioxide is also known as colloidal silica, fumed silica, light anhydrous silicic acid, silicic anhydride and silicon dioxide fumed, among others. In one embodiment, the glidant comprises Aerosil® 200.

Disintegrants that are suitable for use in the pharmaceutical composition of the present invention include, for example, starches, sodium starch glycolate, crospovidone, croscarmellose, microcrystalline cellulose, low substituted hydroxypropyl cellulose, pectins, potassium methacrylate-divinylbenzene copolymer, poly(vinyl alcohol), thylamide, sodium bicarbonate, sodium carbonate, starch derivatives, dextrin, beta cyclodextrin, dextrin derivatives, magnesium oxide, clays, bentonite and mixtures thereof.

The active ingredient, e.g., octreotide or salts thereof, can be mixed with excipients that are pharmaceutically acceptable and compatible with the active ingredient and in amounts suitable for use in the therapeutic methods described herein. Various excipients can be homogeneously mixed with octreotide as would be known to those skilled in the art. Octreotide, for example, can be mixed or combined with excipients such as but not limited to microcrystalline cellulose, colloidal silicon dioxide, lactose, starch, sorbitol, cyclodextrin and combinations of these.

Lubricants that are suitable for use in the pharmaceutical composition of the present invention include agents that act on the flowability of the powder to be compressed include but are not limited to silicon dioxide such as, for example, Aerosil® 200, talc, silica, stearic acid, magnesium stearate, calcium stearate, vegetable stearin, hydrogenated vegetable oils, sodium benzoate, sodium chloride, leucine carbowax, magnesium lauryl sulfate, and glyceryl monostearate.

The invention is further directed to a controlled-release implantable dosage formulation that includes an effective amount a octreotide in a hydrogel, and that, upon administration to a patient or as part of a therapy regimen, provides a release profile (of therapeutically effective blood plasma level of octreotide) extending for a period of at least about two months, about six months or up to about two years.

The dosage formulation can comprise one or more pharmaceutically acceptable excipients. The dosage formulation, for example, can comprise diluents and a lubricant in addition to octreotide unit dose and the rate-controlling polymer. For this purpose, magnesium stearate is a suitable excipient. When these materials are used, the magnesium stearate component can comprise from about 0.5 to about 5% w/w of the dosage formulation (e.g., about 2%), and the hydrogel and octreotide comprise the remainder of the formulation.

Another suitable excipient is hydroxypropylcellulose. When used, the hydroxypropylcellulose component can comprise from about 0.5 to about 20% w/w of the dosage formulation (e.g., about 10%), and the hydrogel and octreotide comprise the remainder of the formulation.

In one embodiment, the formulation comprises both magnesium stearate and hydroxypropylcellulose, e.g., about 2% magnesium stearate and about 10% hydroxypropylcellulose, and the hydrogel and octreotide comprise the remainder of the formulation.

The compositions described herein can be used for the treatment of hormonal diseases characterized by increased levels of GH and IGF-1, e.g., acromegaly, by administering to a patient an implantable formulation of the present invention. The implant can be administered, for example, every about six months, and release a therapeutically effective amount of octreotide. The implantable composition releases a concentration of octreotide in the patient at about the minimum therapeutically effective level to ameliorate the hormonal disorder, yet relatively lower compared to the maximum concentration to enhance restful periods for the patient during the day. The compositions can be administered to a subject at a dose and for a period sufficient to allow the subject to tolerate the dose without showing adverse effects and thereafter increasing the dose of the active agent, if needed, at selected intervals of time until a therapeutic dose is achieved in the subject. The active agent can be administered, for example, at a dose of from about 10 μg to about 1000 μg, about 20 μg to about 800 μg, or about 30 μg to about 300 μg, of octreotide daily for a period of at least about two months, about six months, or up to about two years. The octreotide acetate agent in accordance with the invention is also suitable for the treatment of symptoms associated with carcinoid syndrome and VIPomas.

Additional features and embodiments of the present invention are illustrated by the following non-limiting examples.

EXEMPLIFICATION

Example 1

In Vitro Octreotide Release Rates

This example illustrates preparation of implantable octreotide formulations of the present invention and their in vitro release of octreotide. A series of implants were tested to determine stability and in vitro release characteristics of octreotide from the hydrogel formulations over about 22 weeks (No. 146), 28 weeks (No. 136) and 33 weeks (all other formulations). Each implant contained about 50 milligrams of octreotide acetate and about 2% stearic acid, but the polymer cartridges contained different amounts of HEMA and HPMA and therefore exhibited different % EWCs, as depicted in Table 1.

TABLE 1

| Formulation Number | % HEMA | % HPMA | % EWC | Excipients/Other Ingredients |
|---|---|---|---|---|
| 146 | 0 | 99.5 | 22.9 | 2% stearic acid |
| 145 | 10 | 89.5 | 23.4 | 2% stearic acid |
| 147 | 15 | 84.5 | 24.4 | 2% stearic acid |
| 133 | 20 | 79.5 | 25.2 | 2% stearic acid |
| 144 | 25 | 74.5 | 25.6 | 2% stearic acid |
| 143 | 30 | 69.5 | 26.1 | 2% stearic acid |
| 142 | 35 | 64.5 | 26.6 | 2% stearic acid |
| 136 | 40 | 59.5 | 27.6 | 2% stearic acid |

Figure 2:
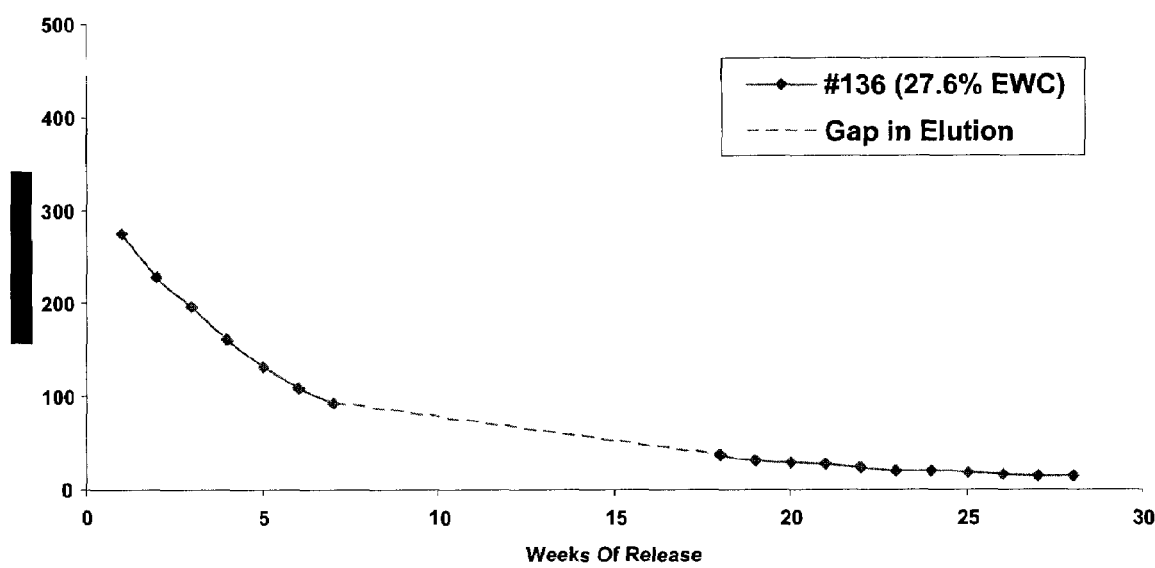
FIG. 2 is a graph showing the release of octreotide from an implant formulation.
Figure 3:
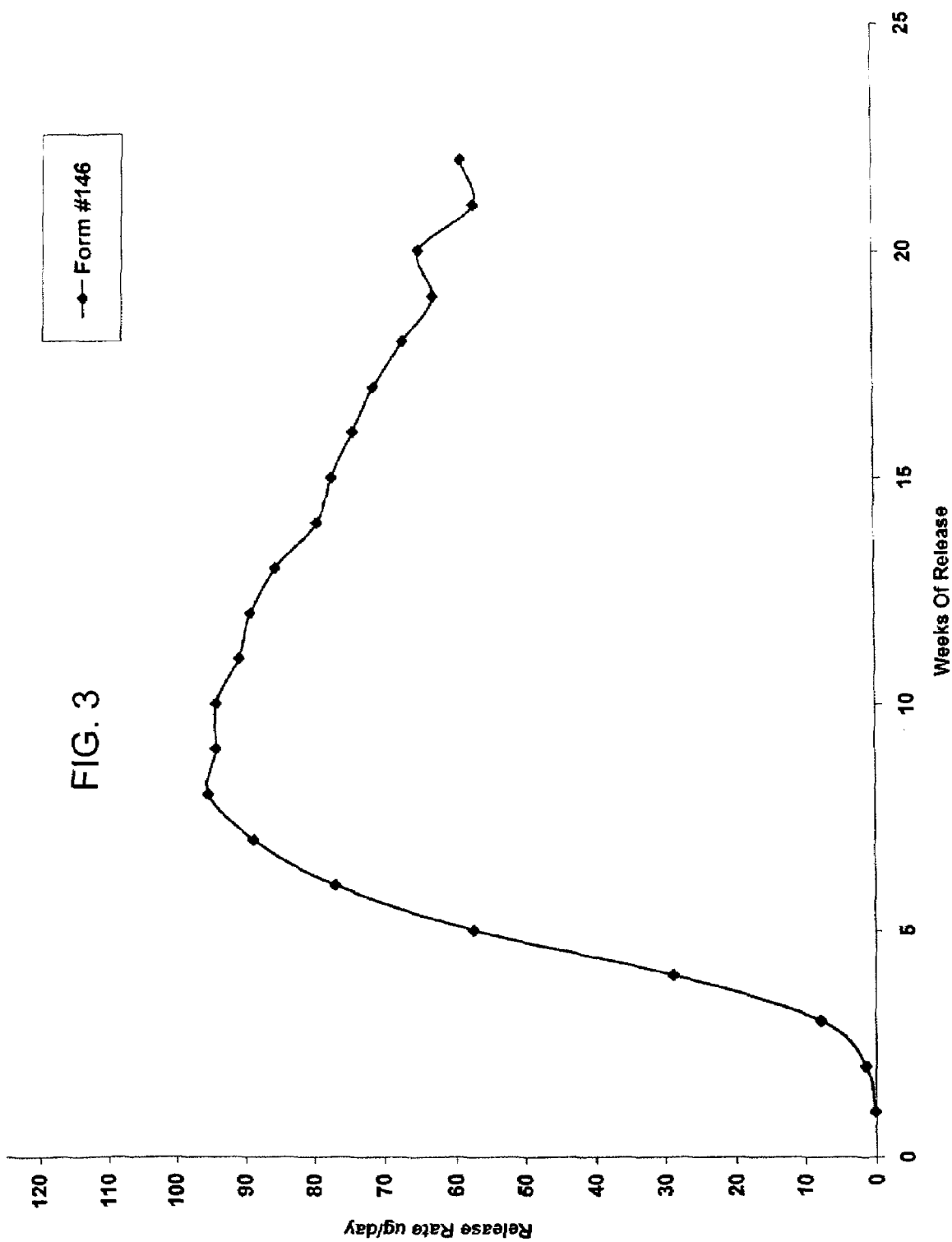
FIG. 3 is a graph showing the release of octreotide from an implant formulation.
Figure 4:
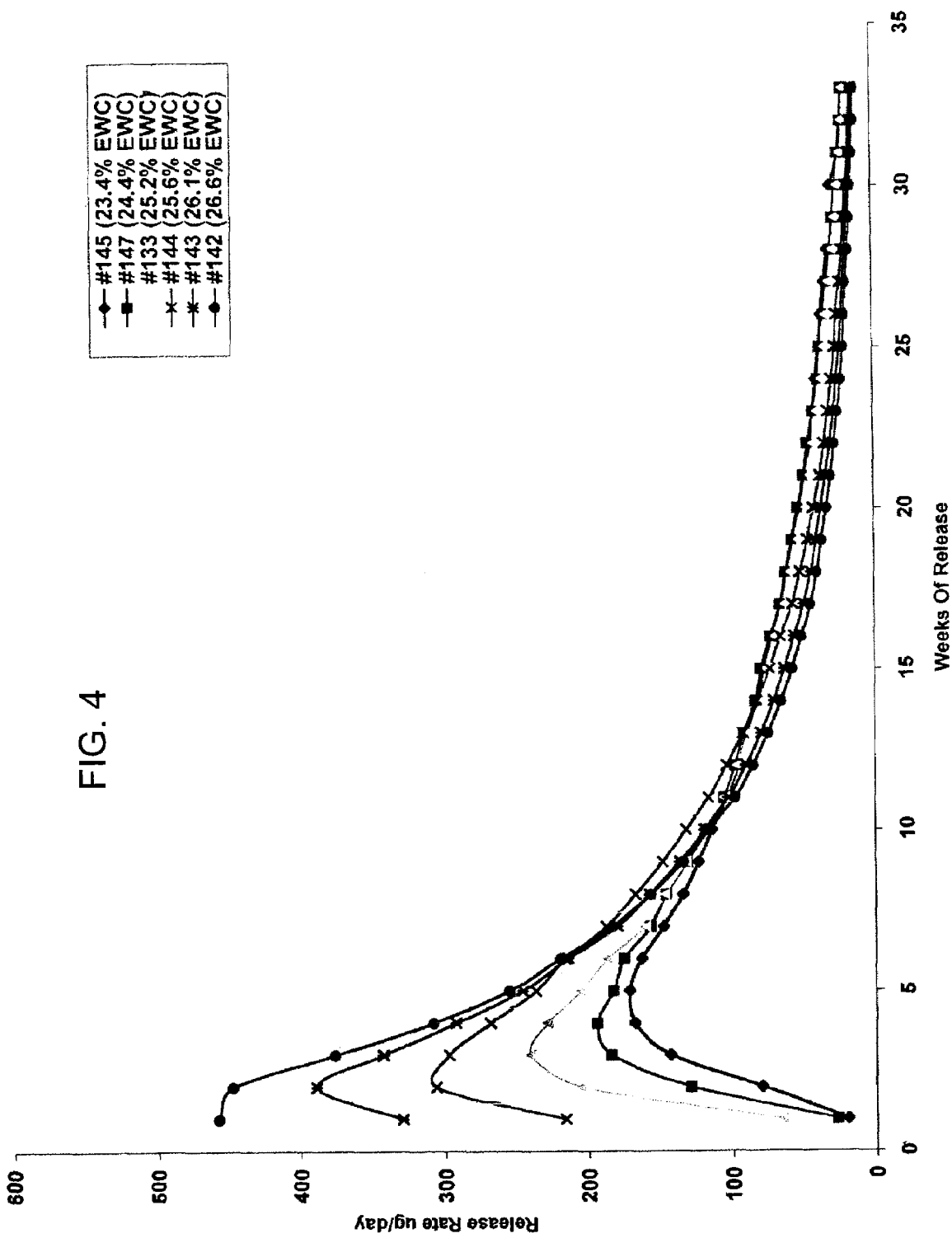
FIG. 4 is a graph showing the release of octreotide from six different implant formulations.

FIGS. 2, 3 and 4 depict the release of octreotide from the implant per day for each of the formulations provided above. As noted in FIG. 2, the initial release is relatively high and drops relatively quickly for Formulation No. 136. As shown in FIG. 3, the initial release rate for Formulation No. 146 is relatively low. FIG. 4 presents the release profiles for Formulation Nos: 145, 147, 133, 144, 143 and 142. As shown in FIG. 4, the initial release rates show a good relationship with the % EWC, ranging from 20 to 450 μg per day for % EWCs of 22.9 to 27.6%. Problems were encountered, however, with respect to the osmotic pressure differential within the implant and the elution media. To stabilize the octreotide formulations, a number of experiments were designed using excipients that would provide better stability based on a "preferential hydration" principle.

Example 2

Formulation Study in Calf Serum

To determine the effect of osmotic pressure on the swelling problem, two implants corresponding to Formulation No. 136 and Formulation No. 143 were eluted in calf serum. In particular, Formulation No. 136, composed of about 40% HEMA and 60% HPMA, containing octreotide acetate with 2% stearic acid and Formulation No. 143, composed of about 30% HEMA and 70% HPMA, containing a mixture of 20% PEG3300 and 80% octreotide acetate, were tested. After three months, the implants exhibited normal appearance, being relatively straight and only slightly swollen.

Example 3

Formulation Study

Due to osmotic pressure differential, the implants described in Example 1 were seen to swell significantly-ultimately resulting in bursting of the implants. This example illustrates formulations designed to screen agents useful in stabilization of the octreotide implant. A series of implants was monitored to determine the effect of excipient on implant shape and durability. Each of the polymer cartridges was composed of about 28% HEMA, about 66.5% HPMA and 5% glycerin. The contents contained octreotide acetate with various excipients, as shown in Table 2.

TABLE 2

| Sample No. | Excipients/Other Ingredients |
|---|---|
| 1 | None |
| 2 | 20% PEG 3300 |
| 3 | 40% PEG 3300 |
| 4 | 2% Stearic acid (control) |
| 5 | 10% Glycolic acid |
| 6 | 20% Poly(lactic acid) |
| 7 | 10% Mannitol |
| 8 | 10% MCC (microcrystalline cellulose) |
| 9 | 20% MCC |
| 10 | 10% Sesame oil |

Hydrophobic agents such as sesame oil and MCC separated in the formulation and did not provide "preferential hydration". Hydrophilic agents like PEG 3300 increased the osmotic pressure differential and increased swelling. Low molecular weight additives like mannitol and glycolic acid did not provide a stabilizing effect and resulted in a decrease in integrity. None of these agents provided satisfactory stabilization of the octreotide formulations.

Example 4

Formulation Study and In Vitro Octreotide Release Rates

This study was conducted to evaluate stability of octreotide in hydrogel implants using various excipients as shown in Table 3. The excipients were chosen to have high molecular weight and some hydrophilic nature. Each implant was made from polymer cartridges composed of about 20% HEMA and about 80% HPMA. The appearance of the implants in saline was monitored and rated over the course of nine weeks. The results are shown in Table 3.

TABLE 3

| Formulation No. | Excipients/Other Ingredients | Implant Appearance at 9 Weeks (see key below) |
|---|---|---|
| 133 | 20% Dextran | 3 |
| 133 | 20% TPGS (vitamin E derivative) | 2 |
| 133 | 20% HEC (hydroxyethyl cellulose) | 3 |
| 133 | 20% HPC (hydroxypropyl cellulose) | 2 |
| 133 | 20% Albumin | 2 |
| 133 | 20% Pectin | 2 |
| 133 | 20% AcDiSol | 1.5 |
| 133 | 20% Carbopol | 1 |
| 133 | 2% SA (stearic acid) - control | 4 |

Figure 5:
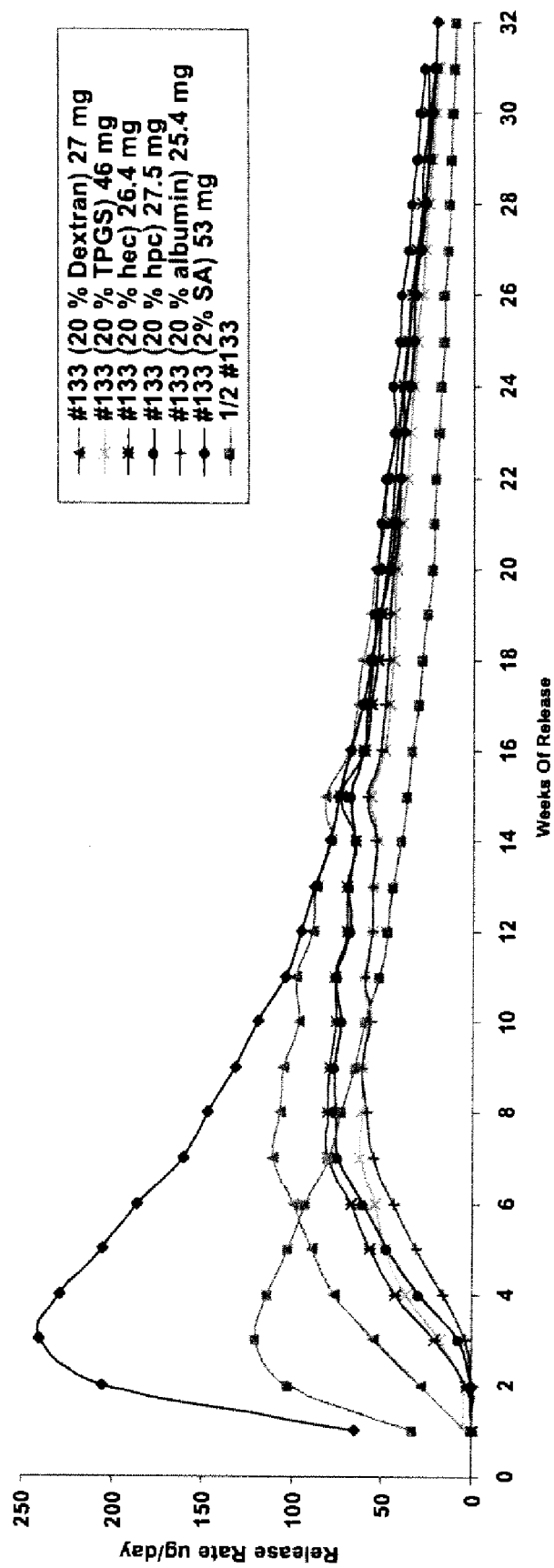
FIG. 5 is a graph showing the release of octreotide from different implant formulations.

As depicted in FIG. 5, the formulation containing dextran had the highest elution rate. The formulations containing pectin, AcDiSol and Carbopol exhibited less than satisfactory release after two weeks hydration and nine weeks elution. Accordingly, desired characteristics including, for example, superior stabilizing effect, combination of good elution and appearance, were achieved with hydroxypropylcellulose.

Example 5

One-Month Implantation Study in a Healthy Dog

This example illustrates preparation of formulations of the present invention and their release of octreotide or pharmaceutically acceptable salts thereof. A healthy dog was implanted with one octreotide subdermal implant. The octreotide subdermal implant formulation had a water content of 26.6%, containing 44 mg octreotide acetate. In vitro release rates were estimated at about 500 µg/day in week 1, decreasing to about 300 µg/day by week 4 for a total release of about 10 mg of octreotide over the duration of the study. The implant was removed at 28 days after implantation. The implant used in this study was about 3.5 cm in length. Blood samples (1.5 mL) to obtain the serum concentration of octreotide acetate, IGF-1 and GH were obtained on days 0, 1-7, 11, 14, 18, 21, 25 and 28 by jugular puncture without anesthesia and without fasting.

Figure 6:
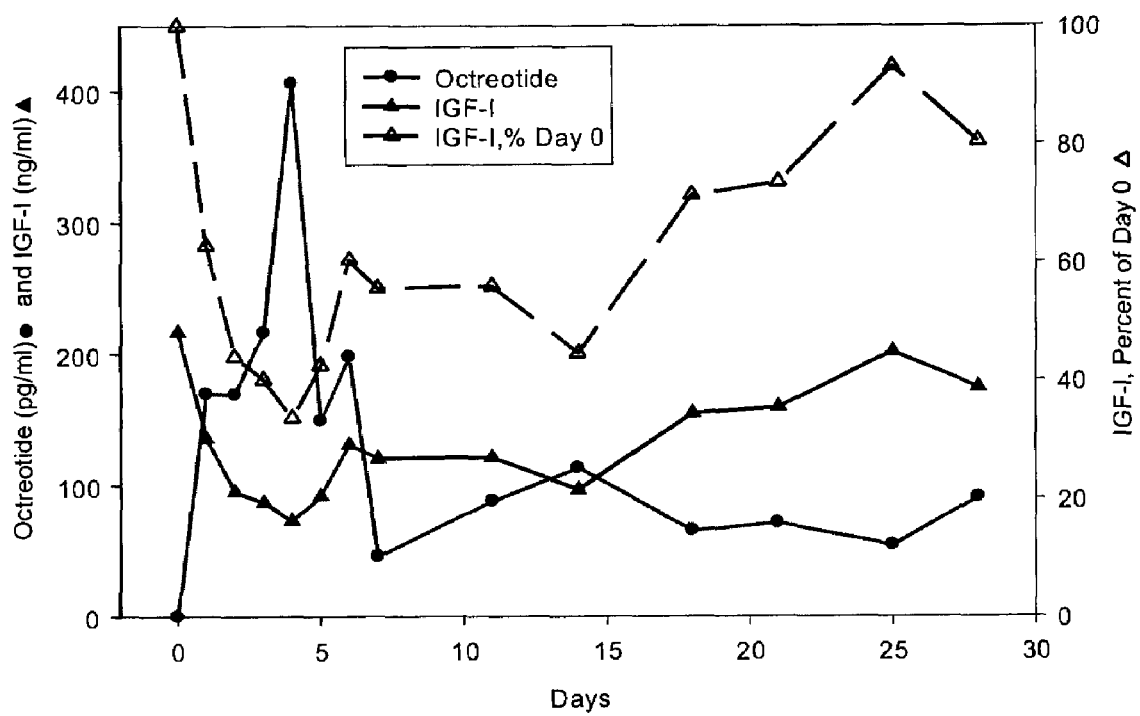
FIG. 6 is a graph showing octreotide and IGF-1 serum levels in a healthy dog implanted with an octreotide formulation.

The octreotide implant formulation was well-tolerated, food intake was normal, and no abnormal behavior was noted. Serum analysis showed a peak of octreotide acetate at day 4 and detectable amounts of octreotide acetate at all intervals measured. IGF-1 concentrations decreased after implantation until day 4, then returned to pre-dose levels by day 25. IGF-1 levels declined from 40 to 90% of pre-implantation level, as can be seen in FIG. 6.

Example 6

Six-Month Implantation Study in Six Healthy Dogs

This example illustrates preparation of formulations of the present invention and their release of octreotide or pharmaceutically acceptable salts thereof. Six healthy dogs were divided into two groups and implanted with one or two octreotide subdermal implants, respectively. The octreotide subdermal implants had a water content of about 25.2% and contained about 60 mg octreotide acetate. The implants were removed six months after implantation. Blood samples (10 mL) to obtain the serum concentration of octreotide acetate, IGF-1 and GH were obtained once daily for the first 7 days following implantation followed by twice a week sampling for three weeks, and then once a week until conclusion of the six month period. Four days prior to implantation, baseline serum samples were taken as a control.

Figure 7:
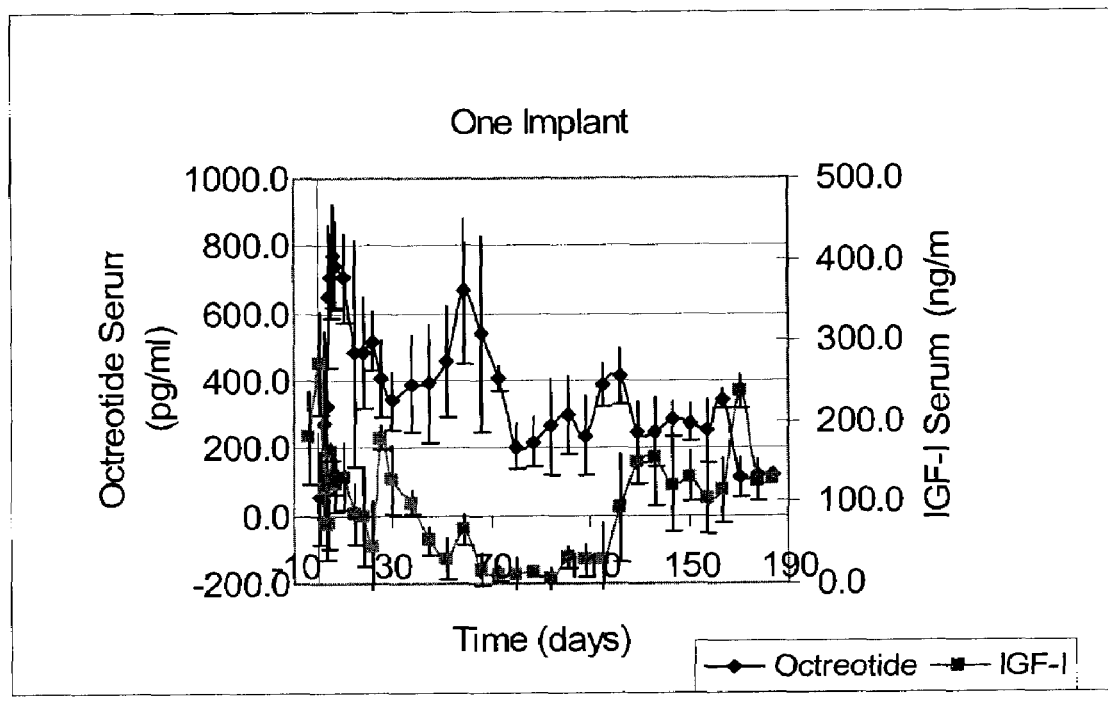
FIG. 7 is a graph showing octreotide and IGF-1 serum levels in a group of three healthy dogs implanted with one octreotide implant formulation over a six month period.
Figure 8:
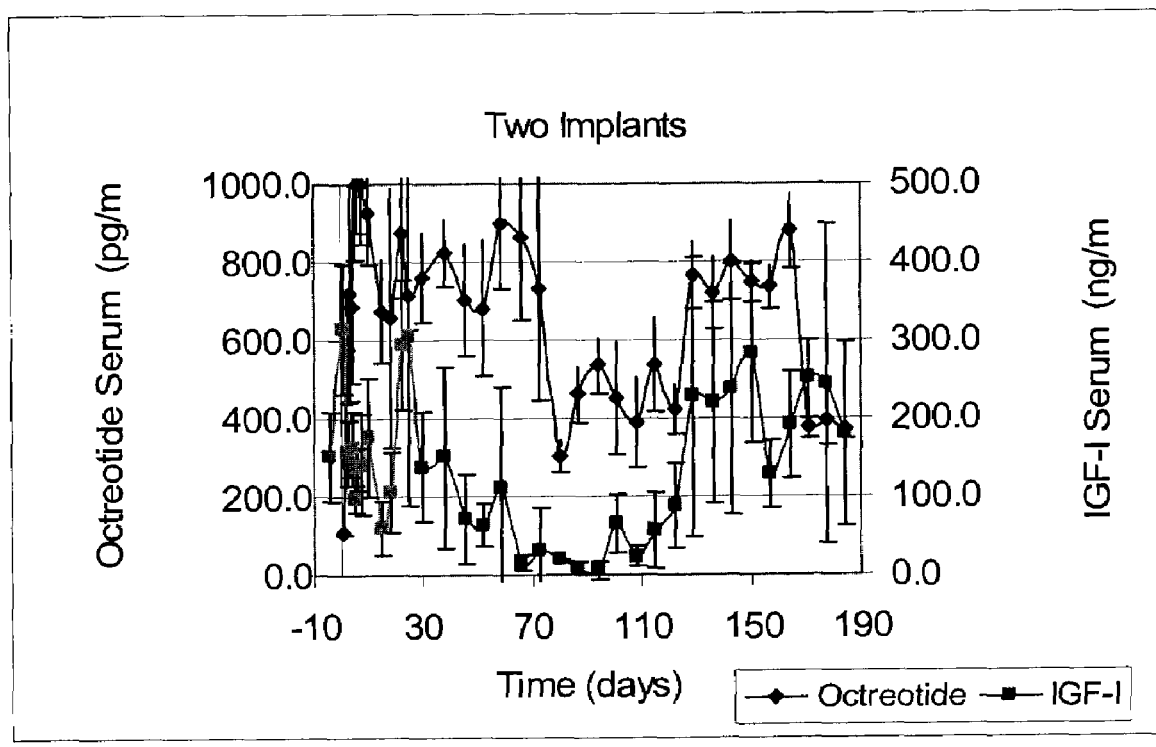
FIG. 8 is a graph showing octreotide and IGF-1 serum levels in a group of three healthy dogs implanted with two octreotide implant formulations over a six month period.

Results indicate octreotide serum levels ranged from 200 to 700 g/mL in dogs receiving one implant and 400 to 1000 μg/mL in dogs receiving two implants. IGF-1 levels were reduced as much as 90% in both treatment groups as can be seen in FIGS. 7 and 8. Measurement of serum GH levels was abandoned after about the first month of the study because levels in healthy animals are too low to detect further reductions. Clinical observations noted the octreotide implant formulation was well-tolerated, food intake was normal, and no abnormal behavior was observed.

Example 7

Six-Month Implantation Study in Humans

This example illustrates preparation of formulations of the present invention and their release of octreotide or pharmaceutically acceptable salts thereof. A six-month study was conducted in eleven patients with acromegaly. One or two implants were implanted subcutaneously in 11 patients diagnosed with acromegaly, who were previously treated with a commercially-available octreotide LAR formulation. Levels of GH and IGF-1 were measured at baseline and every month thereafter for a period of six months. Each implant contained approximately 60 mg of octreotide acetate in a copolymer of 20% HEMA and 79.5% HPMA, with an EWC of about 25.2%. The implants used in this study were about 44 mm in length in a dry state and 50 mm in length in a hydrated state. The diameters of the implants were about 2.8 mm in a dry state and about 3.5 to about 3.6 mm in a hydrated state. The implants were hydrated for a period of about 1 week prior to implantation.

The reference ranges for GH is up to 2.5 mg/L, age-independent. Table 4 illustrates the basal levels of GH in mg/L over six months after implantation of octreotide implants. Patient No. 11 did not participate in the study due to failure to meet screening criteria.

TABLE 4

| Patient | Age | # Implants Rec'd | Screening GH (mg/L) | Visit 1 (Insertion) Basal GH (mg/L) | Visit 2 (Month 1) Basal GH (mg/L) | Visit 3 (Month 2) Basal GH (mg/L) | Visit 4 (Month 3) Basal GH (mg/L) | Visit 5 (Month 4) Basal GH (mg/L) | Visit 6 (Month 5) Basal GH (mg/L) | Visit 7 (Month 6) Basal GH (mg/L) |
|---|---|---|---|---|---|---|---|---|---|---|
| 001 | 39 | 1 | 26 | 16.3 | 0.9 | 1.5 | 1.1 | 1.1 | 1.1 | 2.1 |
| 002 | 38 | 2 | 17.8 | 20.7 | 1.4 | 0.2 | 0.3 | 0.2 | 0.3 | 0.48 |
| 003 | 49 | 1 | 67 | 55 | 2.8 | 3.1 | 3.3 | 5.0 | 5.3 | 5.8 |
| 004 | 47 | 2 | 7.9 | 7 | 2.6 | 3.8 | 2.8 | 3.7 | 4.0 | 2.4 |
| 005 | 43 | 1 | 10.8 | 11 | 2.2 | 1.8 | 2.2 | 1.6 | 2.2 | 1.3 |
| 006 | 43 | 1 | 1.7 | 1.7 | 1.8 | 2.3 | 1.9 | 1.7 | 1.8 | 1.9 |
| 007 | 30 | 2 | 23.3 | 21.8 | 2.4 | 2.2 | 2.9 | 2.0 | 1.1 | 0.51 |
| 008 | 58 | 2 | 1.9 | 3.2 | 0.1 | 0.1 | 2.0 | 0.1 | 0.6 | 0.11 |
| 009 | 47 | 2 | 14.9 | 14.1 | 1.4 | 0.9 | 1.5 | 1.1 | 1.4 | 1.4 |
| 010 | 78 | 1 | 4 | 5.2 | 0.4 | 0.2 | 0.5 | 0.2 | 0.3 | 1.0 |
| 012 | 40 | 2 | 21.1 | 27.8 | 13.5 | 13.7 | 14 | 11.9 | 8.9 | 13.1 |
| mean | | | | 16.7 | 2.7 | 2.7 | 3.0 | 2.6 | 2.7 |  |

By month six, 89% of subjects exhibited normalized growth hormone levels. Reference ranges for IGF-1 are as follows: (i) 17-24 years old about 180-780 ng/mL; (ii) 25-39 years old about 114-400 ng/mL; (iii) 40-54 years old about 90-360 ng/mL; and (iv) >54 years old about 70-290 ng/mL.

Table 5 illustrates the basal levels of IGF-1 in ng/mL over six months after implantation of octreotide implants of the present invention.

TABLE 5

| Patient | Age | # Implants Rec'd | Screening IGF-1 (ng/mL) | Visit 1 (Insertion) IGF-1 (ng/mL) | Visit 2 (Month 1) IGF-1 (ng/mL) | Visit 3 (Month 2) IGF-1 (ng/mL) | Visit 4 (Month 3) IGF-1 (ng/mL) | Visit 5 (Month 4) IGF-1 (ng/mL) | Visit 6 (Month 5) IGF-1 (ng/mL) | Visit 7 (Month 6) IGF-1 (ng/mL) |
|---|---|---|---|---|---|---|---|---|---|---|
| 001 | 39 | 1 | 1500 | 1500 | 820 | 600 | 900 | 880 | 790 | 750 |
| 002 | 38 | 2 | 1700 | 1300 | 210 | 180 | 190 | 170 | 130 | 230 |
| 003 | 49 | 1 | 1100 | 1200 | 610 | 550 | 750 | 660 | 850 | 660 |
| 004 | 47 | 2 | 1700 | 1800 | 1100 | 1200 | 1200 | 1100 | 910 | 990 |
| 005 | 43 | 1 | 1100 | 1000 | 450 | 510 | 480 | 600 | 490 | 430 |
| 006 | 43 | 1 | 520 | 580 | 470 | 430 | 440 | 480 | 440 | 460 |
| 007 | 30 | 2 | 1900 | 1700 | 440 | 560 | 560 | 600 | 430 | 520 |
| 008 | 58 | 2 | 1700 | 1200 | 220 | 240 | 170 | 260 | 160 | 240 |
| 009 | 47 | 2 | 2200 | 1800 | 590 | 830 | 950 | 930 | 1100 | 1100 |
| 010 | 78 | 1 | 590 | 490 | 270 | 260 | 230 | 310 | 220 | 350 |
| 012 | 40 | 2 | 1600 | 1600 | 1300 | 1500 | 1400 | 1700 | 1500 | 1400 |
| mean | | | | 1288 | 589 | 624 | 661 | 699 | 602 | 648 |

By month six, 22% of subjects exhibited a normalized IGF-1 level.

Figure 9A:
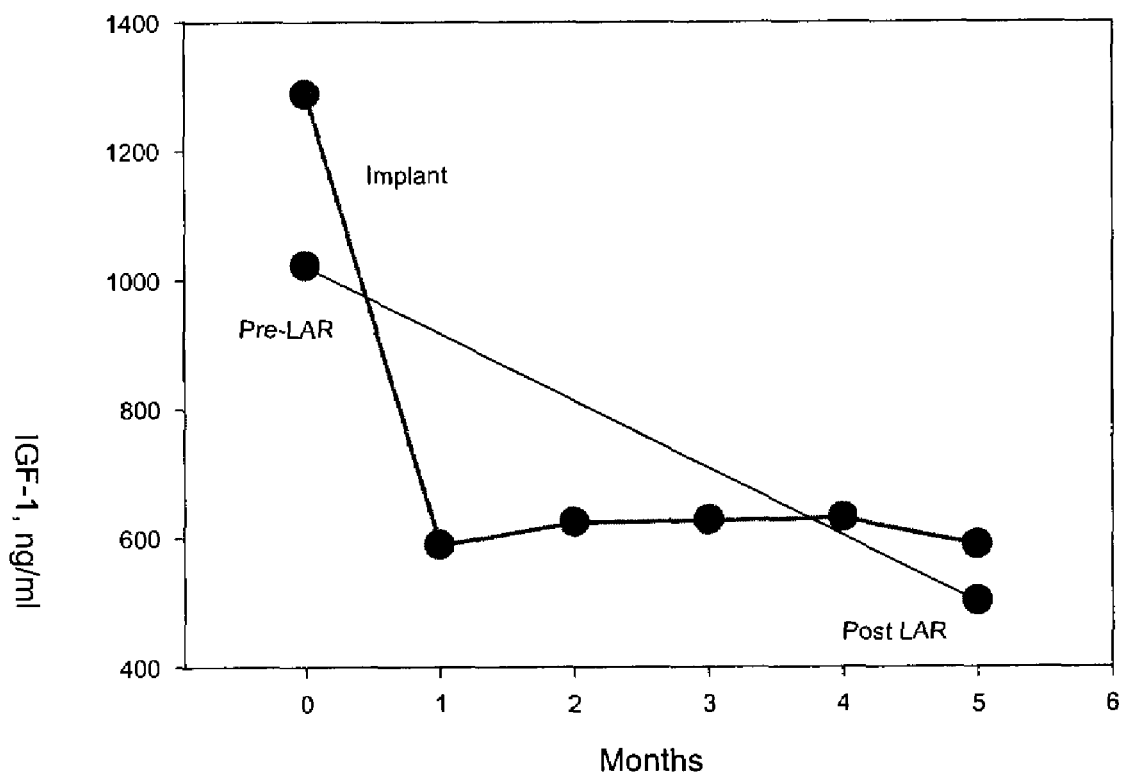
FIGS. 9A and 9B are graphs depicting the IGF-1 serum level and percent change in eleven human subjects with acromegaly over six months implanted with an octreotide formulation.
Figure 9B:
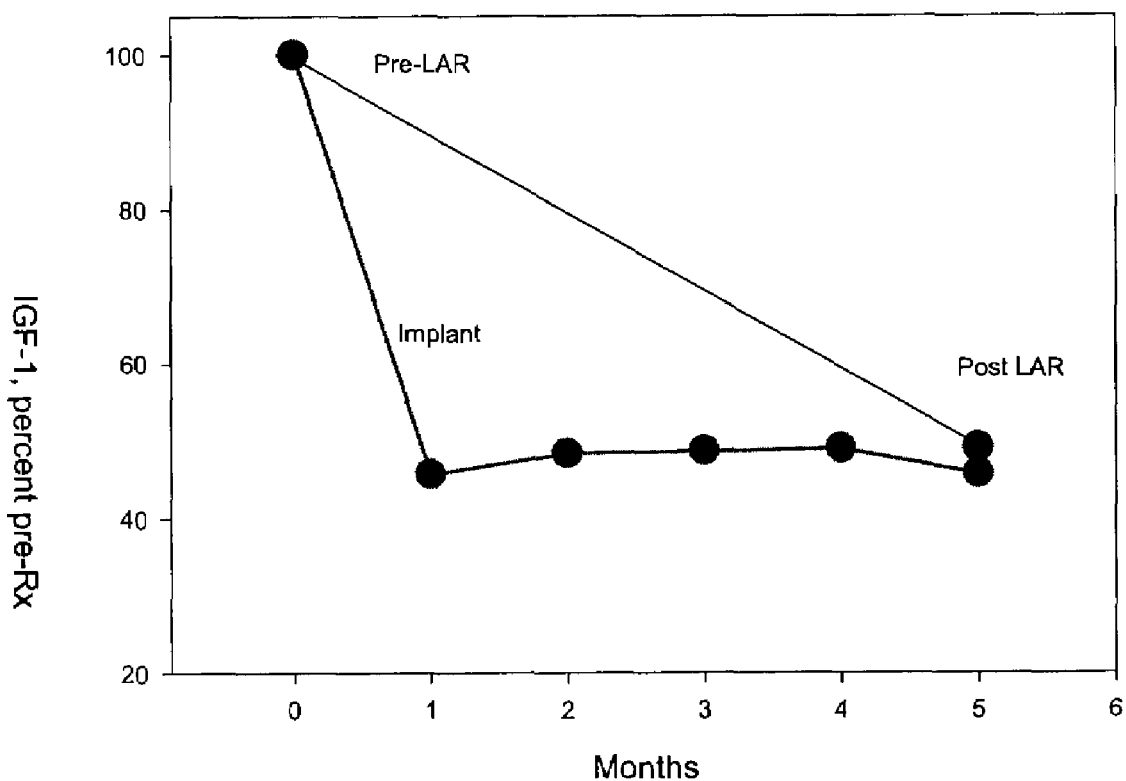

FIGS. 9A and 9B demonstrate a comparison of the octreotide implant with a commercially-available formulation of octreotide acetate. The efficacy of the implant is at least as good as that of the commercially-available octreotide LAR formulation. The therapeutic effect of these implants continued successfully for the entire six months of the study duration.

IGF-1 levels were decreased in all patients, with normalization in two patients. The decrease was already observed at one month of therapy, and the mean IGF-1 level was stable for the following five months. A comparison with decreases previously observed in the same patients while on the commercially available octreotide LAR formulation therapy was possible in eight of the nine patients. In six of the eight patients, the percentage decrease in IGF-1 during the implant was greater than that while on the commercially-available octreotide LAR formulation, whereas in two, it was less. After 6 months of therapy with the implant, GH levels in 3 patients were <1 ng/mL and in another 5, were <2.5 ng/mL. This compares favorably with the results of the commercially-available octreotide LAR formulation, where GH levels in only 2 patients were <1 ng/mL and in another 2, were under 2.5 ng/mL.

Levels of octreotide in the serum of patients was also measured, as shown in Table 6.

TABLE 6

| | | Month | | | | | | | |
|---|---|---|---|---|---|---|---|---|---|
| #Implants | Patient ID | 1 Visit 2 | 2 Visit 3 | 3 Visit 4 | 4 Visit 5 | 5 Visit 6 | 6 Visit 7 | 7 Visit 8 | Gender |
| 1 | Patient 1 | 1181 | 874.5 | 738.0 | 894.3 | 699.2 | 722.3 | 169.0 | F |
| 2 | Patient 2 | 2686 | 2478 | 1625 | 1833 | 1388 | 1203 | 280 | M |
| 1 | Patient 3 | 2570 | 2351 | 1332 | 980.5 | 1131 | 775.2 | 173 | F |
| 2 | Patient 4 | 4268 | 3308 | 2582 | 2650 | 2455 | 1984 | 166 | M |
| 1 | Patient 5 | 1218 | 1022 | 610.0 | 783.2 | 709.4 | 545.8 | 144 | F |
| 1 | Patient 6 | 1899 | 1445 | 1427 | 1123 | 1148 | 747.7 | 206 | F |
| 2 | Patient 7 | 5524 | 2621 | 3656 | 3141 | 2205 | 1466 | 154 | F |
| 2 | Patient 8 | 8684 | 3387 | 4899 | 3336 | 3454 | 1765 | 170 | F |
| 2 | Patient 9 | 3850 | 860.6 | 2638 | 1766 | 1729 | 1510 | 203 | M |
| 1 | Patient 10 | 2055 | 1628 | 1192 | 863.9 | 1641 | 1231 | 1130 | F |
| 2 | Patient 12 | 2527 | 1366 | 2006 | 962.8 | 1484 | 1156 | 189 | M |

Figure 10:
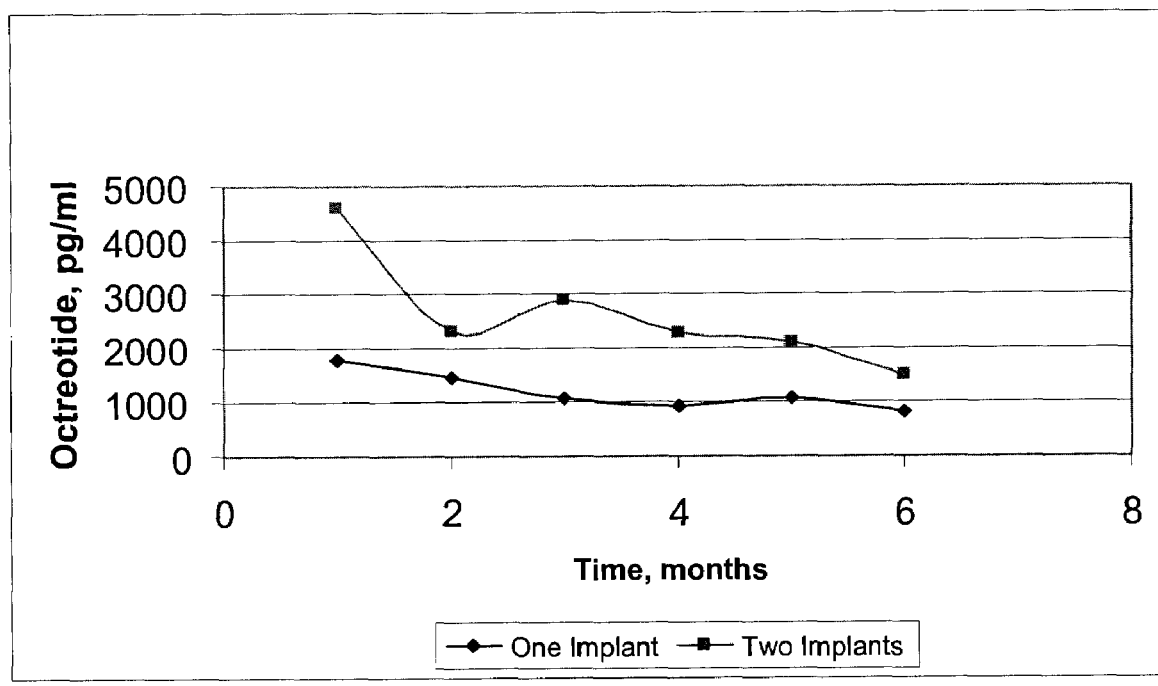
FIG. 10 is a graph depicting octreotide serum levels in eleven human subjects with acromegaly over six months implanted with an octreotide formulation.

A comparison of the octreotide levels achieved with one and two implants is depicted in the graph in FIG. 10. Overall, results indicated that the octreotide implant is at least as effective as the commercially available LAR formulation of octreotide acetate in reducing GH levels and IGF-1 levels in patients with acromegaly.

Example 8

In Vitro Octreotide Delivery Using Dry Implants

This example illustrates preparation of formulations and their release of octreotide or pharmaceutically acceptable salts thereof. Two healthy dogs were implanted with one octreotide subdermal implant of the present invention. The implants were not hydrated prior to implantation. The octreotide subdermal implants were composed of about 59.5% HPMA and about 40% HEMA and had an equilibrium water content of 27.6%. The implants contained about 84 mg of octreotide acetate, hydroxypropylcellulose and magnesium stearate. The implants were removed six months after implantation. Blood samples (10 mL) were drawn to obtain the serum concentration of octreotide acetate and IGF-1 once daily every other day for the first four weeks following implantation followed by twice a week sampling for four weeks, and then once a week until conclusion of the six month period. Two days prior to implantation, baseline serum samples were taken as a control.

Figure 11:
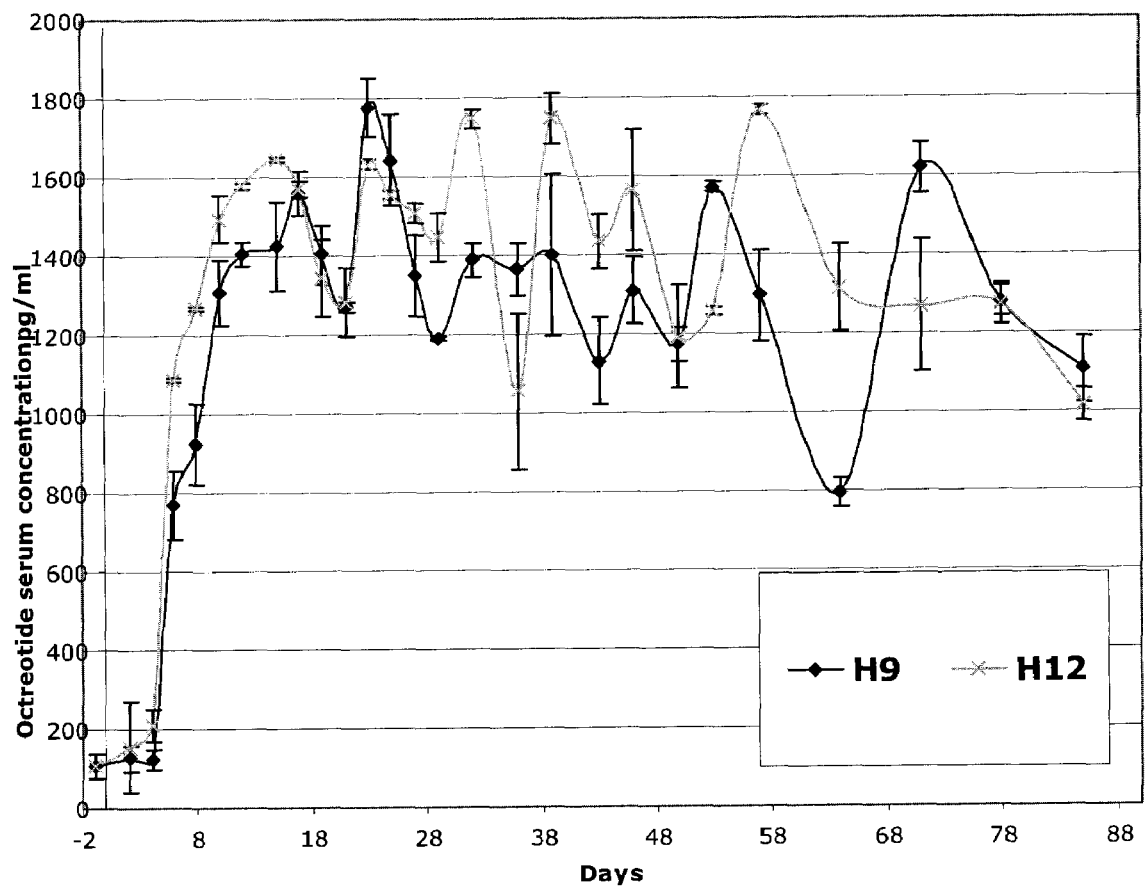
FIG. 11 is a graph depicting octreotide serum levels in two dogs over six months implanted with an octreotide formulation.
Figure 12:
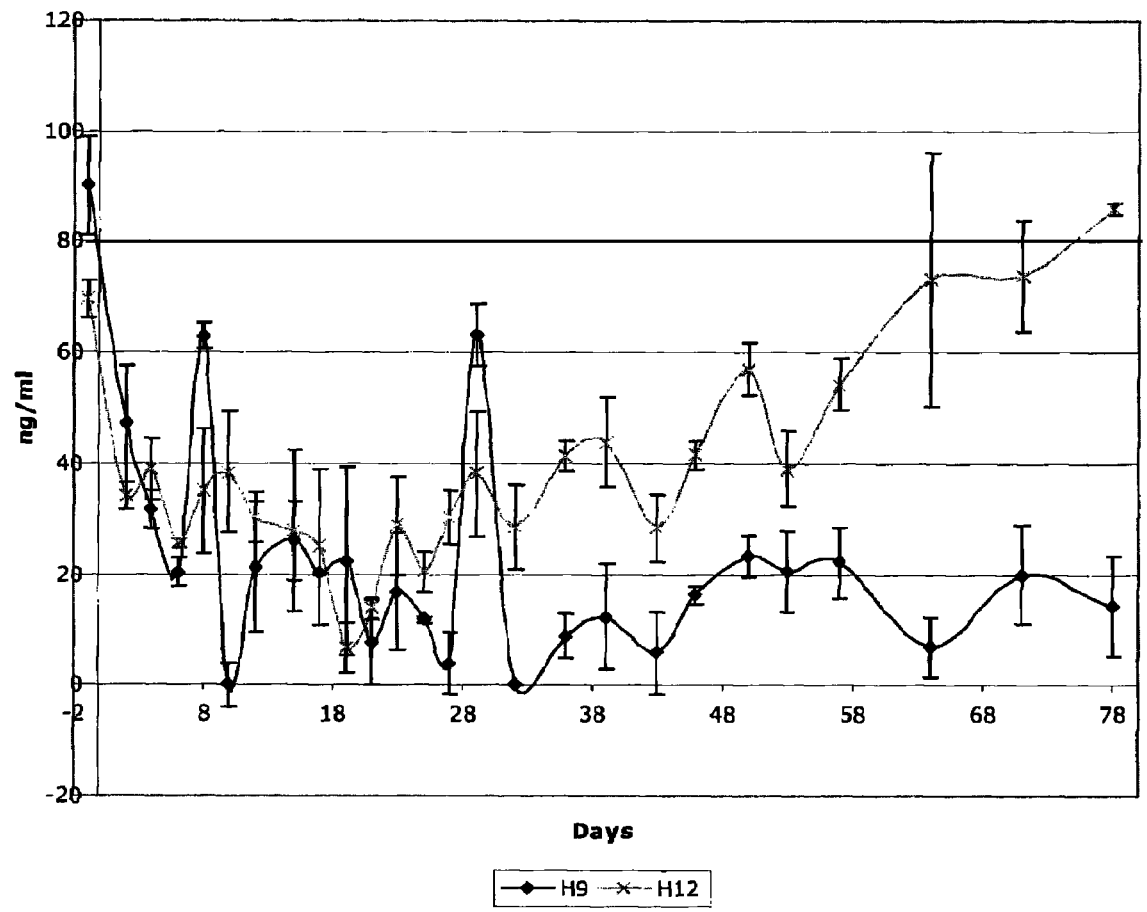
FIG. 12 is a graph depicting IGF-1 serum levels in two dogs over six months implanted with an octreotide formulation.

FIG. 11 shows the octreotide levels in the serum of the dogs and FIG. 12 shows the levels of IGF-1 in the dogs.

Example 9

Implant Compositions

Possible compositions for the implants, for example, those listed in Table 7, were tested. Implant cartridges greater than about 3.2-3.4 mm (dry) are aided by the use of release agents, e.g., vitamin E TPGS, during the formation process.

TABLE 7

| | Composition of Implant | |
|---|---|---|
| | Small Implant | Large Implant |
| API | 60 mg Octreotide Acetate | 84 mg Octreotide Acetate |

TABLE 7-continued

| | Composition of Implant | |
|---|---|---|
| | Small Implant | Large Implant |
| Pellet Excipients | 10% Hydroxypropyl cellulose (~6.8 mg/implant) | 10% Hydroxypropyl cellulose (~9.5 mg/implant) |
| | 2% Magnesium Stearate (~1.3 mg/implant) | 2% Magnesium Stearate (~2 mg/implant) |
| Monomer Mixture Composition | 20% HEMA | 40% HEMA |
| | 79.5% HPMA | 59.5% HPMA |
| | 0.5% TMPTMA | 0.5% TMPTMA |
| | Added to mixture: | Added to mixture: |
| | 1% Triton X-100 | 1% Vitamin E TPGS |
| | 0.3% BME | 0.3% BME |
| | 0.1% P-16 | 0.1% P-16 |
| Dry Implant Size | 2.8 mm × 43 mm | 3.4 mm × 43 mm |
| Surface Area | 378 mm$^2$ | 459 mm$^2$ |
| Hydrated Implant Size | 3.4 mm × 50 mm | 4.3 mm × 50 mm |
| Surface Area | 534 mm$^2$ | 675 mm$^2$ |
| EWC | 26.0% | 28.7% |

TABLE 7-continued

| | Composition of Implant | |
|---|---|---|
| | Small Implant | Large Implant |
| Sterilization | Gamma Irradiation | Gamma Irradiation |
| Packaging Solution | Implants packaged dry in 2 compartment package with 0.9% saline solution in the second compartment. Implant is combined with saline 7-14 days prior to implantation to allow for implant hydration. | Implants packaged dry in 2 compartment package with 0.9% saline solution in the second compartment. Implant is combined with saline 3-7 days prior to implantation to allow for implant hydration. |
| Packaging | Divided Pouch with LF4835W Foil Barrier/FR5500 PET/PE Clear Sleeve as components. LF4835W - DMF # 15796 FR5500 - Approved for food contact | Divided Pouch with JT48FLLP Foil Barrier/IT-CB259B Aluminum Oxide CTD PET Clear Sleeve as components. For use in sterile medical packaging |
| Average Daily Release Rate | 130 µg/day for 6 months | 250 µg/day for 6 months |

Example 10

An Open-Label Study to the Evaluate the Pharmacokinetic and Pharmacodynamic Response of a Hydrated and Non-Hydrated 84 mg Octreotide Implant in Patients with Acromegaly Approximately 30 patients with acromegaly were enrolled after written informed consent was obtained. Patients were divided in 2 groups per the study randomization schedule: 15 patients received one hydrated 84 mg octreotide implant and 15 patients received one non-hydrated 84 mg octreotide implant. Eligible patients received the implant within 7 days of their screening visit. The octreotide implant was inserted subcutaneously in the inner aspect of their non-dominant arm under local anesthesia. Blood samples for the determination of IGF-1, GH and octreotide serum concentrations were collected at predetermined time points within the first 6 weeks after implantation. Patients then return for visits at Week 8, 12, 16, 20 and 24 to have blood samples collected for the determination of IGF-1, GH and octreotide serum concentrations, as well as safety assessments. At the end of the 6-month (24-week) treatment phase, the implant is removed. Following implant removal, the patient is instructed to return in 4 weeks for the End of Study Visit (Week 28). Safety and efficacy is carefully monitored throughout the study.

Investigational Products

Hydrated octreotide implant (84 mg octreotide acetate) for subcutaneous implantation Non-hydrated octreotide implant (84 mg octreotide acetate) for subcutaneous implantation Duration of Treatment Eligible patients receive one implant, either hydrated or non-hydrated. At the end of the 6-month (24-week) treatment phase, the implant is removed.

Criteria for Inclusion

1. Male and female patients with acromegaly
2. Must be ≧18 years of age
3. Confirmed diagnosis of a growth hormone-secreting tumor (elevation of IGF-1 level ≧20% above upper limit of age- and sex-adjusted normal value and either a post-glucose GH of ≧1.0 ng/mL or a pituitary tumor demonstrable on MRI). If patient has undergone pituitary surgery and has residual tumor present, it must be at least 3 mm in distance from the optic chiasm (unless patient is not a surgical candidate) and IGF-1 level must be elevated as described above. If no residual tumor is present or patient is inoperable then patient must meet both IGF-1 and GH criteria as described above.
4. Must be either a full or partial responder to octreotide demonstrated by historical laboratory values, as defined below:
   a. Full responder: suppression of serum IGF-1 to normal age- and sex-adjusted levels and suppression of serum GH to <1.0 ng/mL after OGTT
   b. Partial responder: a ≧30% decrease in IGF-1 and GH values when compared to pre-treatment values, but not meeting criteria for full responder OR
   c. Must be a responder to octreotide demonstrated by laboratory values obtained via an acute aqueous test during the Screening Visit for octreotide naïve patients or patients in whom response to octreotide is unknown, as defined below:
   d. Responder via acute aqueous test: a ≧30% decrease in GH values at any time point of the 4 hour test period in response to a subcutaneous injection of 100∝γ of aqueous octreotide
5. Must be able to communicate, provide written informed consent, and willing to participate and comply with study requirements
6. Patient is eligible to participate in the opinion of the Investigator Criteria for Exclusion 1. Women who are pregnant, lactating, or of child-bearing potential who are not practicing a medically acceptable method of birth control
2. Patients with pituitary surgery less than 12 weeks prior to screening
3. Patients with liver disease (e.g., cirrhosis, chronic active or persistent hepatitis or persistent abnormalities of ALT, AST (level>2× normal), alkaline phosphatase (level>2× normal), or direct bilirubin (level>1.5× normal)
4. Other laboratory values considered by the Investigator or Sponsor to be clinically significant
5. Patients with unstable angina, sustained ventricular arrhythmias, heart failure (NYHA III and IV), or a history of an acute myocardial infarction within 3 months of screening
6. Patients with symptomatic cholelithiasis
7. Patients with a history of drug or alcohol abuse within 6 months of screening
8. Patients who have received any investigational drug within 1 month of screening
9. Patients receiving radiotherapy for their pituitary tumor at any time before screening
10. Patients who have discontinued octreotide due to tolerability or efficacy issues.

Figure 13:
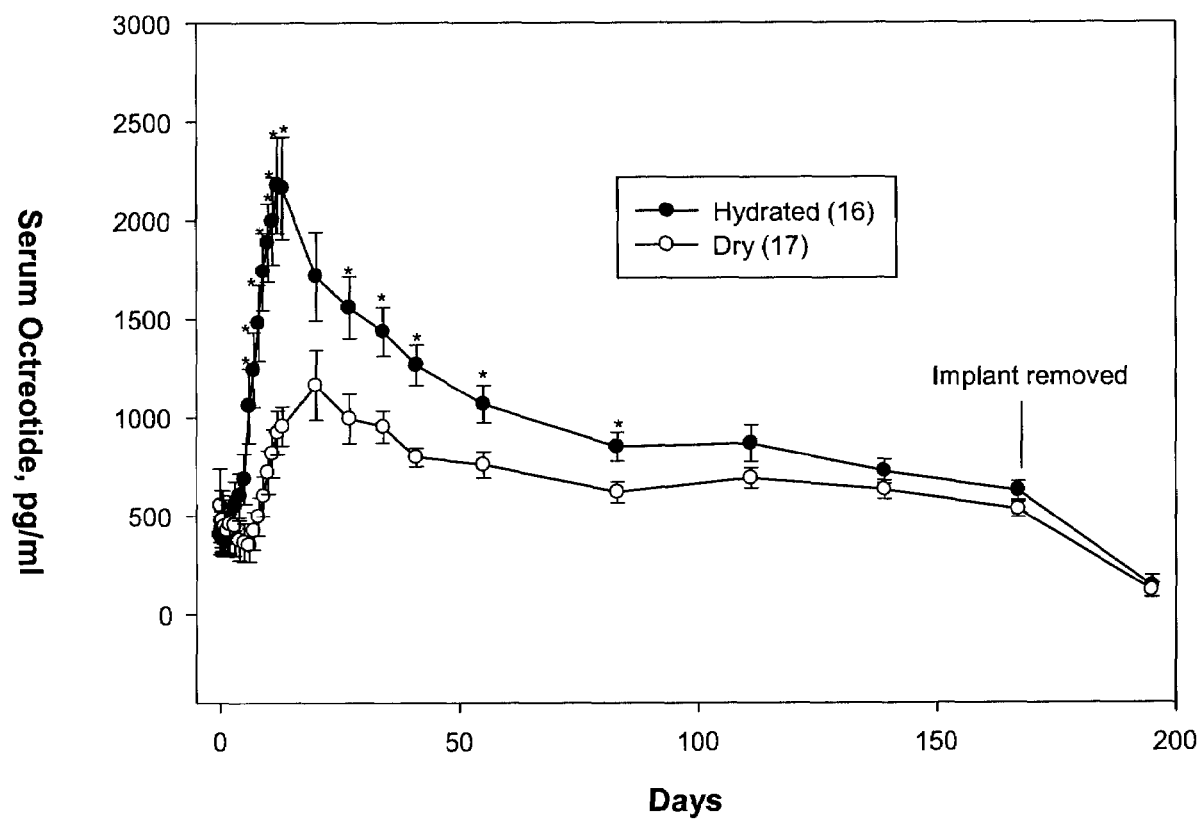
FIG. 13 is a graph showing serum octreotide levels after hydrated implant delivery and dry implant delivery (see also Table 6).
Figure 14:
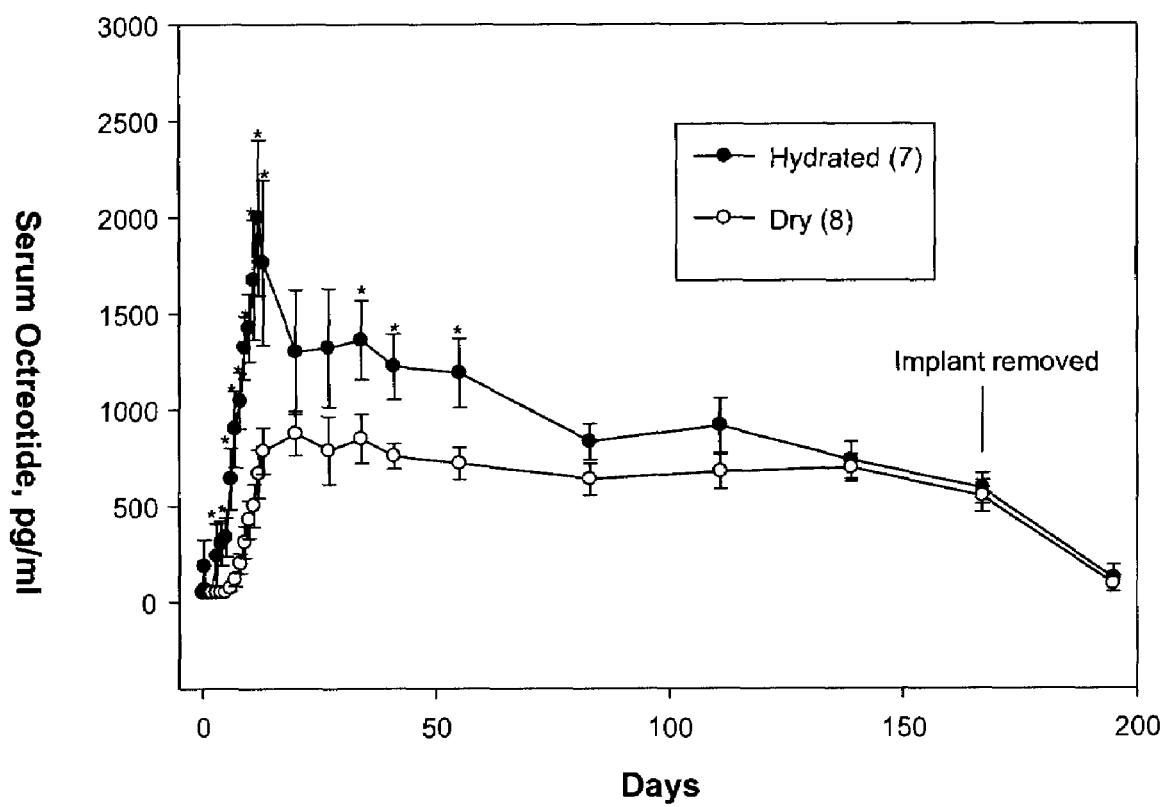
FIG. 14 is a graph showing serum octreotide levels after hydrated implant delivery and dry implant delivery (see also Table 6).
Figure 15A:
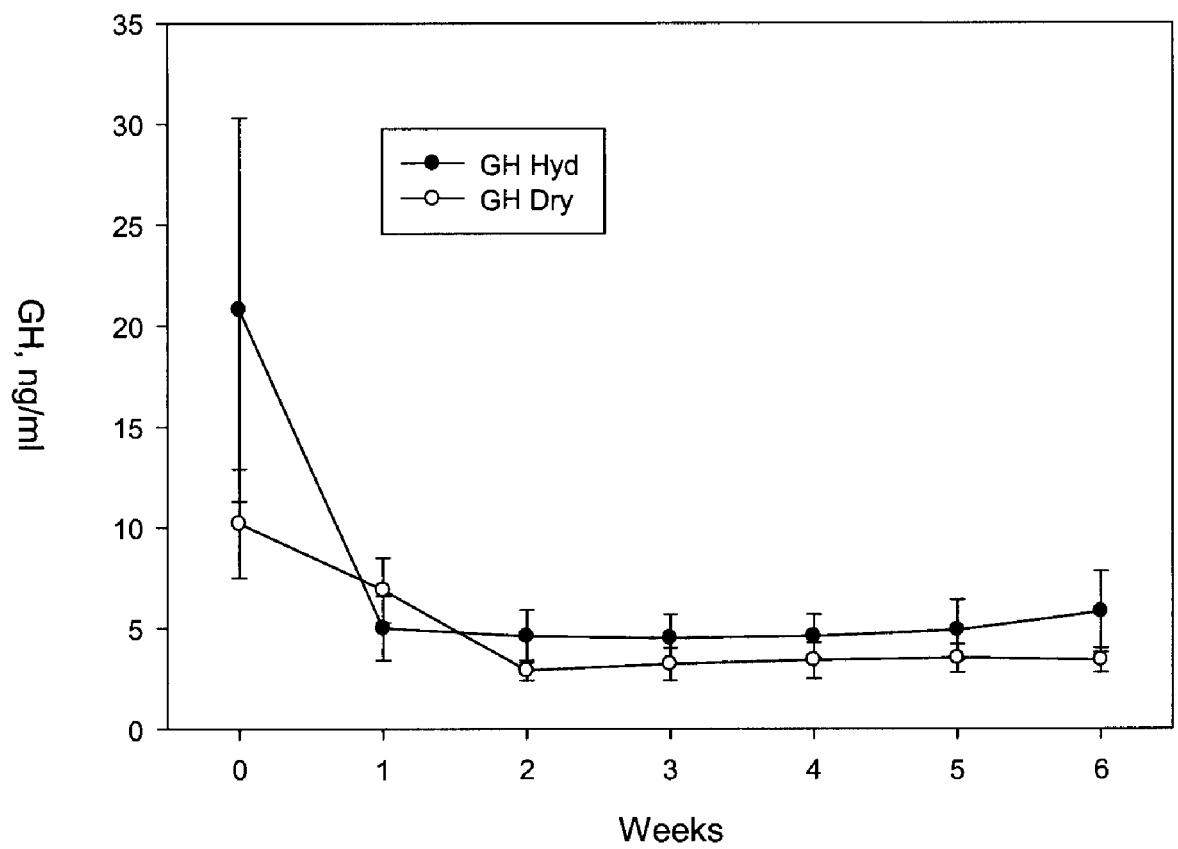
FIGS. 15A and 15B are graphs showing the level of growth hormone after delivery of octreotide by hydrated and dry implants (GH concentration, upper panel; % GH decrease, bottom panel).
Figure 15B:
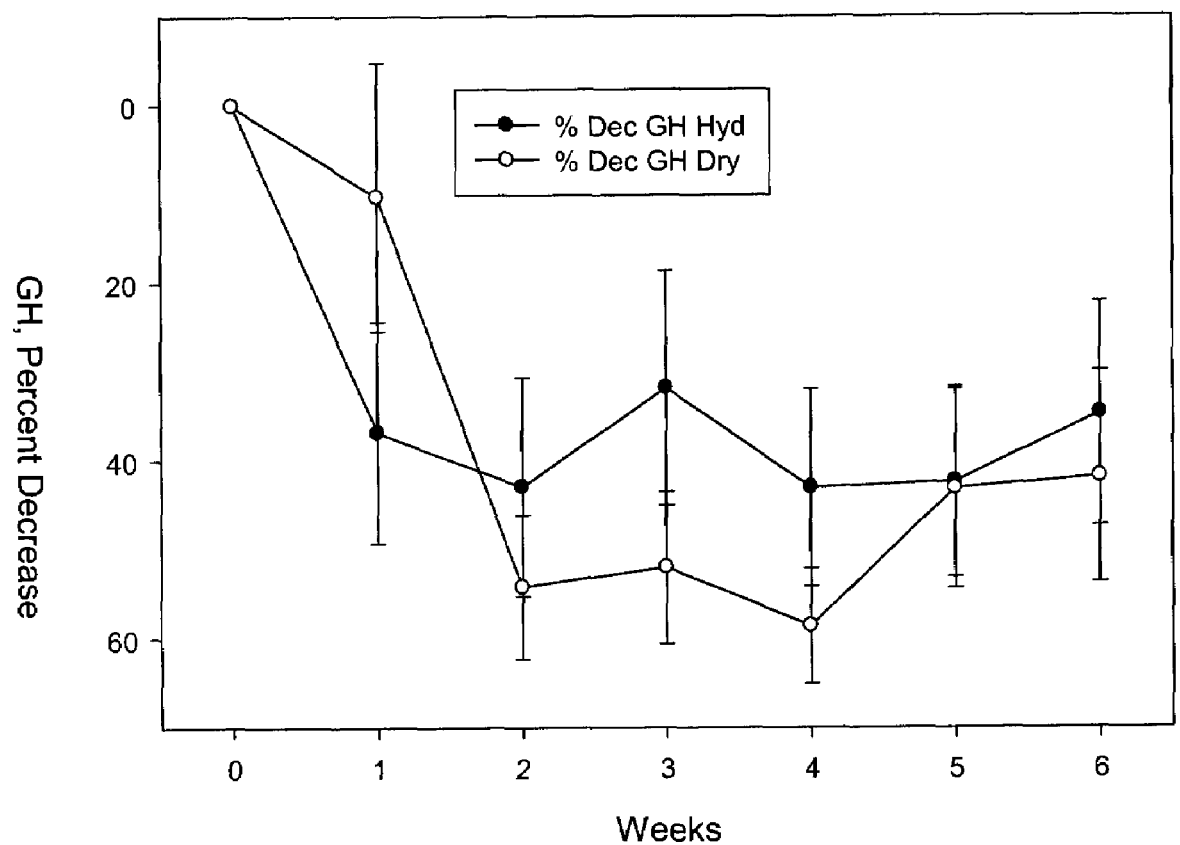
Figure 16A:
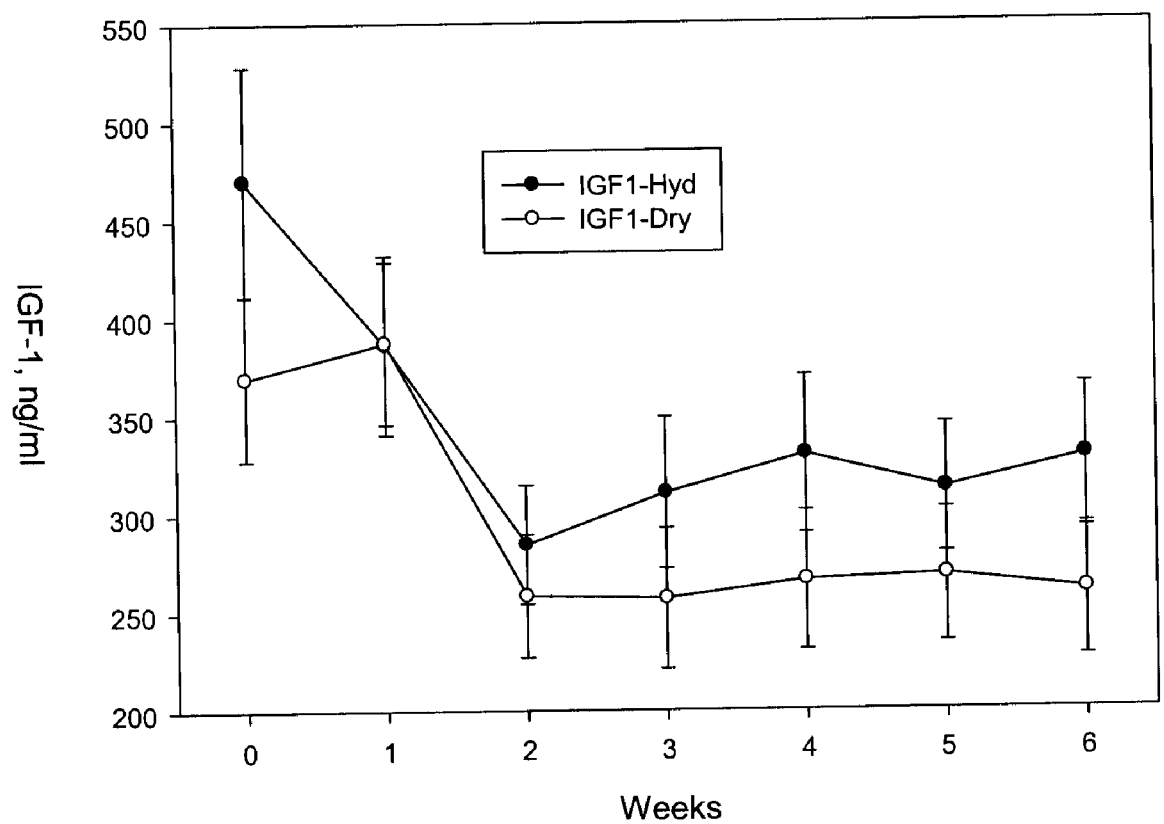
FIGS. 16A and 16B are graphs showing the level of IGF-1 after delivery of octreotide by hydrated and dry implants (IGF-1 concentration, upper panel; standard deviation, bottom panel).
Figure 16B:
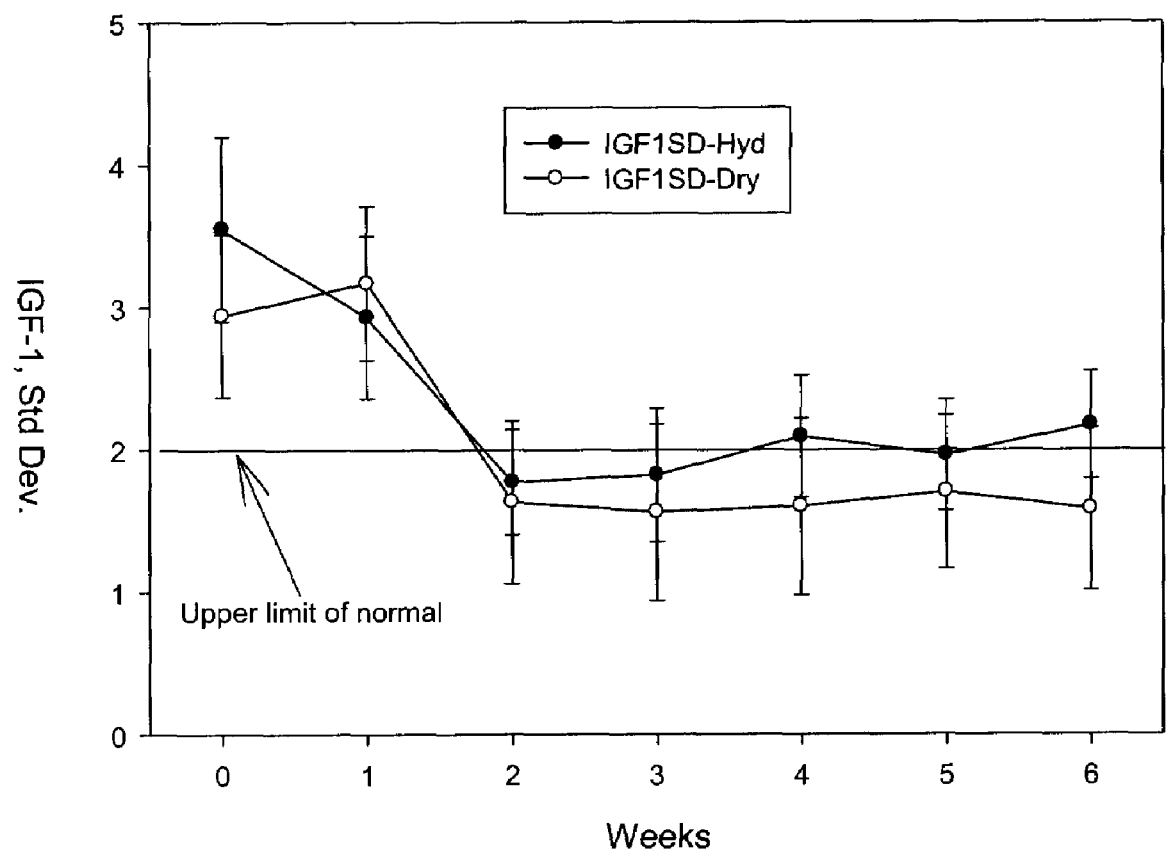
Figure 17A:
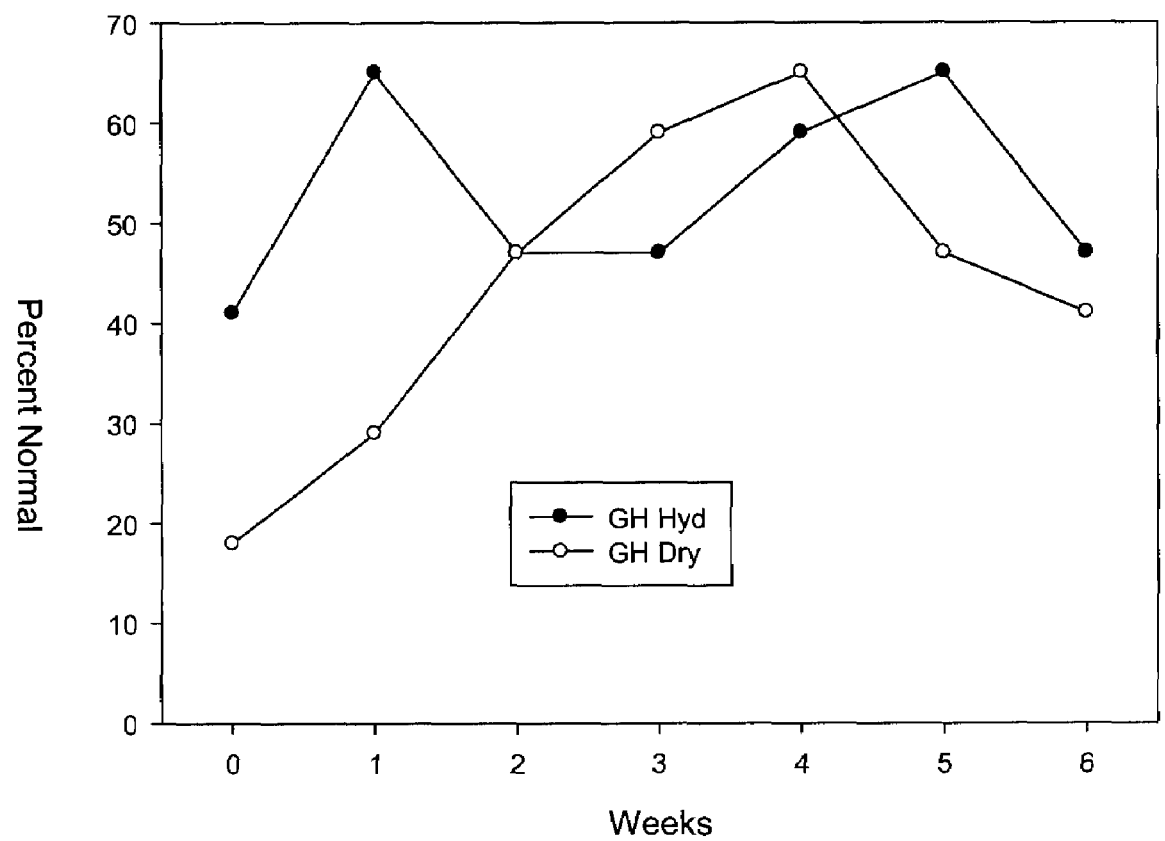
FIGS. 17A and 17B are graphs showing the level of IGF-1 after delivery of octreotide by hydrated and dry implants (both panels show data from studies with values expressed as the percent of normal IGF-1 levels).
Figure 17B:
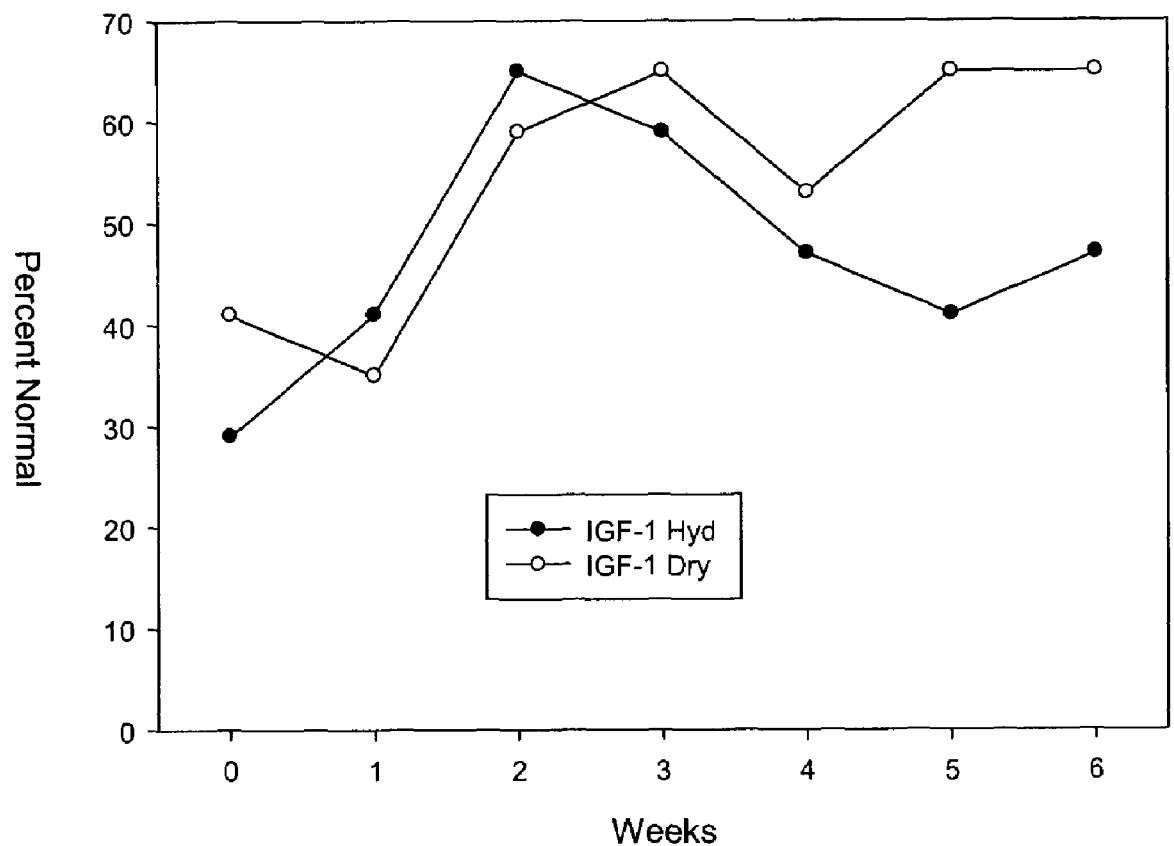

Serum levels of octreotide were determined (see FIGS. 13 and 14 for graphical data). The efficacy of cytokine concentration modulation after the octreotide implant was inserted, either in the dry form or after hydration, is shown in FIGS. 15, 16 and 17.

Example 11

An Open-Label Study to the Evaluate the Pharmacokinetic and Pharmacodynamic Response of a Hydrated and Non-Hydrated 84 mg Octreotide Implant in Patients with Carcinoid Syndrome Patients with carcinoid syndrome are enrolled in the study after written informed consent is obtained. Patients are divided into two groups per the study randomization schedule, with the first group receiving one hydrated 84 mg octreotide implant and the second group receiving one non-hydrated 84 mg octreotide implant. Eligible patients receive the implant within 7 days of their screening visit. The octreotide implant is inserted subcutaneously in the inner aspect of their non-dominant arm under local anesthesia. Blood samples for the determination of IGF-1, GH and octreotide serum concentrations are collected at predetermined time points within the first 6 weeks after implantation. Patients then return for visits at Week 8, 12, 16, 20 and 24 to have blood samples collected for the determination of IGF-1, GH and octreotide serum concentrations, as well as safety assessments. At the end of the 6-month (24-week) treatment phase, the implant will be removed. Following implant removal, the patient will be instructed to return in 4 weeks for the End of Study Visit (Week 28). Safety and efficacy will be carefully monitored throughout the study.

Investigational Products

Hydrated octreotide implant (84 mg octreotide acetate) for subcutaneous implantation
Non-hydrated octreotide implant (84 mg octreotide acetate) for subcutaneous implantation Duration of Treatment Eligible patients receive one implant, either hydrated or non-hydrated. At the end of the 6-month (24-week) treatment phase, the implant is removed. Following implant removal, the patient is instructed to return in 4 weeks for the End of Study Visit.

Criteria for Inclusion

1. Male and female patients with carcinoid syndrome
2. Must be ≧18 years of age
3. Confirmed diagnosis of carcinoid syndrome, with patient showing elevated urinary 5-HIAA (5-hydroxindole acetic acid) levels, low blood tryptophan, and high blood chromaogranin A and serotonin, as assessed by standard medical diagnostic assays.
4. Must be able to communicate, provide written informed consent, and willing to participate and comply with study requirements
5. Patient is eligible to participate in the opinion of the Investigator Criteria for Exclusion 1. Women who are pregnant, lactating, or of child-bearing potential who are not practicing a medically acceptable method of birth control
2. Patients with pituitary surgery less than 12 weeks prior to screening
3. Patients with liver disease (e.g., cirrhosis, chronic active or persistent hepatitis or persistent abnormalities of ALT, AST (level>2× normal), alkaline phosphatase (level>2× normal), or direct bilirubin (level>1.5× normal)
4. Other laboratory values considered by the Investigator or Sponsor to be clinically significant
5. Patients with unstable angina, sustained ventricular arrhythmias, heart failure (NYHA III and IV), or a history of an acute myocardial infarction within 3 months of screening
6. Patients with symptomatic cholelithiasis
7. Patients with a history of drug or alcohol abuse within 6 months of screening
8. Patients who have received any investigational drug within 1 month of screening
9. Patients receiving radiotherapy for their pituitary tumor at any time before screening
10. Patients who have discontinued octreotide due to tolerability or efficacy issues.

Serum levels of octreotide are determined for each patient. During treatment, each patient is examined for a reduction in flushing episodes and other symptoms characteristic of carcinoid syndrome exhibited by the patient before treatment, and examined for reduced median 24 hr urinary 5-HIAA levels.

Although the present invention has been described in considerable detail with reference to certain preferred embodiments thereof, other versions are possible. Therefore the spirit and scope of the appended claims should not be limited to the description and the preferred versions contained within this specification.

What is claimed is:

1. A formulation for the controlled release of octreotide after implantation into a subject comprising a preparation substantially encased in methacrylate-based hydrophilic polymers, wherein the preparation comprises octreotide, wherein the formulation is effective to permit release of octreotide at a rate of about 30 µg to about 800 µg per day over about six months in vivo, and wherein the hydrophilic polymer but not the preparation further comprises a release agent with a molecular weight of at least about 1000 Daltons.

2. The formulation of claim 1, wherein the release agent is a non-ionic surfactant.

3. The formulation of claim 2, wherein the non-ionic surfactant comprises a polyethylene glycol hydrophilic tail and a lipophilic head.

4. The formulation of claim 1, wherein the release agent is selected from the group consisting of: Brij 35, polyoxyethylene(20)sorbitan trioleate, Tween 20, Tween 80, Vitamin E TPGS, and a mixture of any two or more thereof.

5. The formulation of claim 1, wherein the release agent has a molecular weight of at least about 1200 Daltons.

6. The formulation of claim 1, wherein the hydrophilic polymer has an exterior surface area of about 350 mm² or greater.

7. The formulation of claim 6, wherein the hydrophilic polymer has an exterior surface area ranging from about 350 mm² to about 1500 mm².

8. The formulation of claim 1, wherein the formulation permits release of octreotide at an average rate ranging from about 75 µg per day to about 300 µg per day in vivo.

9. The formulation of claim 8, wherein the formulation provides an in vivo average $C_{ss}$ of about 0.1 ng/mL to about 9 ng/mL of octreotide in the subject.

10. The formulation of claim 9, wherein the formulation provides an in vivo average $C_{ss}$ of about 1 ng/mL to about 4 ng/mL of octreotide in the subject.

11. The formulation of claim 1, wherein the octreotide is octreotide acetate.

12. The formulation of claim 1, wherein the hydrophilic polymer comprises a mixture of 2-hydroxyethyl methacrylate and hydroxypropyl methacrylate.

13. The formulation of claim 12, wherein the hydrophilic polymer comprises a mixture of about 20% of 2-hydroxyethyl methacrylate and about 80% hydroxypropylmethacrylate.

14. The formulation of claim 12, wherein the hydrophilic polymer comprises a mixture of about 40% of 2-hydroxyethyl methacrylate and about 60% hydroxypropylmethacrylate.

15. The formulation of claim 1, wherein the preparation comprises about 40 mg to about 120 mg of octreotide.

16. The formulation of claim 15, wherein preparation comprises about 50 mg of octreotide acetate.

17. The formulation of claim 15, wherein the preparation comprises about 85 mg of octreotide acetate.

18. The formulation of claim 1, wherein the preparation further comprises an excipient selected from the group consisting of: magnesium stearate, stearic acid, vegetable stearin, talc and silica.

19. The formulation of claim 1, wherein the preparation further comprises a compound selected from the group consisting of: hydroxypropylcellulose, hydroxyethyl cellulose, methyl cellulose, sodium carboxymethyl cellulose, modified starch and crosslinked polyvinyl pyrrolidone.

20. A method of decreasing GH levels or IGF-1 levels in a subject and/or treating an octreotide-sensitive disease, disorder or symptom, the method comprising subcutaneously implanting at least one dry implantable device comprising a preparation encased in a hydrophilic polymer, wherein the preparation comprises octreotide, and wherein the hydrophilic polymer but not the preparation further comprises a release agent having a molecular weight of at least 1000.

21. The method of claim 20, wherein the preparation comprises about 40 mg to about 120 mg of octreotide acetate.

22. The method of claim 20, wherein two implantable devices are implanted subcutaneously.

23. The method of claim 20, wherein the implantable device remains implanted in a patient for a continuous time period ranging from about six months to about two years.

24. The method of claim 23, wherein the implantable device remains implanted in the patient for a continuous time period ranging from about six months to about one year.

25. The method of claim 20, wherein the implantable device is sterilized by irradiation.

26. The method of claim 20, wherein the octreotide-sensitive disease, disorder or symptom is selected from the group consisting of:
  acromegaly or symptoms associated with acromegaly, a symptom associated with a carcinoid tumor, VIPoma or neuroendocrine tumor, carcinoid syndrome, proliferative diabetic retinopathy, rosacea, pancreatitis, gastrointestinal bleeding, pancreatic and intestinal fistulas, Graves-Basedow ophthalmopathy, glaucoma, and/or corneal disease associated with vasularization treating acromegaly or symptoms associated with acromegaly.

27. The method of claim 26, wherein a symptom associated with a carcinoid tumor, VIPoma or neuroendocrine tumor is selected from the group consisting of severe diarrhea, watery diarrhea or flushing episodes.

28. A kit comprising a formulation for the controlled release of octreotide after implantation into a subject comprising a preparation substantially encased in methacrylate-based hydrophilic polymers, wherein the preparation comprises octreotide, wherein the formulation is effective to permit release of octreotide at a rate of about 30 µg to about 800 µg per day over about six months in vivo, and wherein the hydrophilic polymer but not the preparation further comprises a release agent with a molecular weight of at least about 1000 Daltons.

\* \* \* \* \*